United States Patent
Wattebled et al.

(10) Patent No.: US 9,555,148 B2
(45) Date of Patent: Jan. 31, 2017

(54) SUPERABSORBING POLYMERS WITH RAPID ABSORPTION PROPERTIES AND METHOD FOR PRODUCING THE SAME

(71) Applicant: EVONIK DEGUSSA GMBH, Essen (DE)

(72) Inventors: Laurent Wattebled, Dusseldorf (DE); Jorg Harren, Baesweiler (DE); Matthias Naumann, Hamburg (DE); Franck Furno, Heiligenhaus (DE); Matthias Lobert, Essen (DE); Rainer Teni, Moers (DE)

(73) Assignee: Evonik Degussa GmbH, Essen (DE)

( * ) Notice: Subject to any disclaimer, the term of this patent is extended or adjusted under 35 U.S.C. 154(b) by 25 days.

(21) Appl. No.: 14/352,091

(22) PCT Filed: Nov. 12, 2012

(86) PCT No.: PCT/EP2012/072352
§ 371 (c)(1),
(2) Date: Apr. 16, 2014

(87) PCT Pub. No.: WO2013/072268
PCT Pub. Date: May 23, 2013

(65) Prior Publication Data
US 2014/0312273 A1    Oct. 23, 2014

(30) Foreign Application Priority Data

Nov. 17, 2011   (DE) .................. 10 2011 086 516

(51) Int. Cl.
| | | |
|---|---|---|
| *C08J 3/24* | (2006.01) | |
| *A61L 15/24* | (2006.01) | |
| *A61L 15/22* | (2006.01) | |
| *B01J 20/30* | (2006.01) | |
| *B01J 20/26* | (2006.01) | |
| *C08F 216/14* | (2006.01) | |
| *C08F 220/06* | (2006.01) | |
| *A61L 15/60* | (2006.01) | |
| *C08F 222/10* | (2006.01) | |

(52) U.S. Cl.
CPC ............. *A61L 15/225* (2013.01); *A61L 15/24* (2013.01); *A61L 15/60* (2013.01); *B01J 20/267* (2013.01); *B01J 20/3064* (2013.01); *C08F 220/06* (2013.01); *C08J 3/245* (2013.01); *C08F 216/1416* (2013.01); *C08F 222/1006* (2013.01); *C08J 2333/02* (2013.01)

(58) Field of Classification Search
None
See application file for complete search history.

(56) References Cited

U.S. PATENT DOCUMENTS

| | | | |
|---|---|---|---|
| 4,076,663 A | | 2/1978 | Masuda et al. |
| 4,179,367 A | | 12/1979 | Barthell et al. |
| 4,286,082 A | | 8/1981 | Tsubakimoto et al. |
| 4,587,308 A | | 5/1986 | Makita et al. |
| 5,118,719 A | | 6/1992 | Lind |
| 5,154,713 A | * | 10/1992 | Lind .................. A61L 15/425 210/691 |
| 5,154,743 A | | 10/1992 | Takato et al. |
| 5,236,965 A | | 8/1993 | Engelhardt et al. |
| 5,314,420 A | * | 5/1994 | Smith ............... A61F 13/15203 210/691 |
| 5,399,591 A | | 3/1995 | Smith et al. |
| 5,409,771 A | | 4/1995 | Dahmen et al. |
| 5,451,613 A | | 9/1995 | Smith et al. |
| 5,610,220 A | | 3/1997 | Klimmek et al. |
| 5,672,633 A | | 9/1997 | Brehm et al. |
| 5,712,316 A | | 1/1998 | Dahmen et al. |
| 5,985,944 A | | 11/1999 | Ishizaki et al. |
| 5,989,446 A | | 11/1999 | Hicks et al. |
| 5,994,440 A | | 11/1999 | Staples et al. |

(Continued)

FOREIGN PATENT DOCUMENTS

| | | |
|---|---|---|
| CN | 1889987 A | 1/2007 |
| CN | 102906135 A | 1/2013 |

(Continued)

OTHER PUBLICATIONS

Bub et al., U.S. Appl. No. 14/195,104, filed Mar. 3, 2014.
Fricker et al., U.S. Appl. No. 14/136,934, filed Dec. 20, 2013.
German language International Search Report mailed on Jan. 15, 2013 in PCT/EP2012/072352 (3 pages).
International Search Report mailed on May 8, 2005 in PCT/US2004/04229 (4 pages).
Tian et al., U.S. Appl. No. 13/860,019, filed Apr. 10, 2013.
Tian et al., U.S. Appl. No. 14/157,769, filed Jan. 17, 2014.
Tian et al., U.S. Appl. No. 14/161,962, filed Jan. 23, 2014.

(Continued)

*Primary Examiner* — Joseph D Anthony
(74) *Attorney, Agent, or Firm* — Bernard Lau; Linda S. Li; Jason S. Ngui

(57) ABSTRACT

This invention relates to a method for producing a water-absorbing polymer, including the following steps: (i) mixing ($\alpha$1) 0.1 to 99.999 wt % polymerizable, ethylenically unsaturated, acid-group-containing monomers; ($\alpha$2) 0 to 70 wt % polymerized ethylenically unsaturated, monomers copolymerizable with ($\alpha$1); ($\alpha$3) 0.00 1 to 10 wt %, cross-linking agent(s); ($\alpha$4) 0 to 30 wt % water-soluble polymers; and ($\alpha$5) 0 to 20 wt % additive(s), wherein the total quantity by weight of ($\alpha$1) to ($\alpha$5) amounts to 100 wt %, (ii) radical polymerization while cross-linking, in order to form a hydrogel polymer, (iii) drying the hydrogel polymer, (iv) grinding and sifting the water-absorbing polymer, (v) surface post-cross-linking the hydrogel polymer, and (vi) drying and processing the polymer, wherein, before the admixture of the initiator and the start of radical polymerization, 0.01 to 5 wt % of a surfactant, relative to acrylic acid, 0.01 to 5 wt % foaming agent, are added.

16 Claims, No Drawings

(56) References Cited

U.S. PATENT DOCUMENTS

| | | |
|---|---|---|
| 6,090,875 A | 7/2000 | Staples et al. |
| 6,107,358 A * | 8/2000 | Harada .................. C08F 2/10 521/133 |
| 6,124,391 A | 9/2000 | Sun et al. |
| 6,136,873 A | 10/2000 | Haehnle et al. |
| 6,245,252 B1 | 6/2001 | Hicks et al. |
| 6,251,960 B1 | 6/2001 | Ishizaki et al. |
| 6,441,266 B1 | 8/2002 | Dyer et al. |
| 6,562,879 B1 | 5/2003 | Hatsuda et al. |
| 6,565,981 B1 | 5/2003 | Messner et al. |
| 6,605,673 B1 | 8/2003 | Mertens et al. |
| 6,620,889 B1 | 9/2003 | Mertens et al. |
| 6,623,848 B2 | 9/2003 | Brehm et al. |
| 6,831,142 B2 | 12/2004 | Mertens et al. |
| 6,972,011 B2 | 12/2005 | Maeda et al. |
| 7,163,966 B2 | 1/2007 | Joy et al. |
| 7,169,843 B2 | 1/2007 | Smith et al. |
| 7,179,862 B2 | 2/2007 | Mertens et al. |
| 7,285,599 B2 | 10/2007 | Mertens et al. |
| 7,572,864 B2 | 8/2009 | Mertens et al. |
| 7,615,579 B2 | 11/2009 | Joy et al. |
| 7,625,957 B2 | 12/2009 | Harren et al. |
| 7,728,079 B2 | 6/2010 | Harren et al. |
| 7,795,345 B2 | 9/2010 | Smith et al. |
| 7,812,082 B2 | 10/2010 | McIntosh et al. |
| 7,833,624 B2 | 11/2010 | Harren et al. |
| 7,939,597 B2 | 5/2011 | Bub et al. |
| 8,048,942 B2 | 11/2011 | Fricker et al. |
| 8,063,121 B2 | 11/2011 | Fricker et al. |
| 8,071,202 B2 | 12/2011 | Furno et al. |
| 8,076,436 B2 | 12/2011 | Braig et al. |
| 8,198,385 B2 | 6/2012 | Gartner et al. |
| 8,222,477 B2 | 7/2012 | Azad et al. |
| 8,236,884 B2 | 8/2012 | Smith et al. |
| 8,247,499 B2 | 8/2012 | Walden et al. |
| 8,252,873 B1 | 8/2012 | Gartner et al. |
| 8,258,249 B2 | 9/2012 | Bub et al. |
| 8,304,369 B2 | 11/2012 | Tian et al. |
| 8,349,913 B2 | 1/2013 | Harren et al. |
| 8,357,766 B2 | 1/2013 | Fricker et al. |
| 8,403,904 B2 | 3/2013 | Tian et al. |
| 8,420,567 B1 | 4/2013 | Naumann et al. |
| 8,440,300 B2 | 5/2013 | Sharavanan et al. |
| 8,445,596 B2 | 5/2013 | Mertens et al. |
| 8,466,228 B2 | 6/2013 | Smith et al. |
| 8,476,189 B1 | 7/2013 | Naumann et al. |
| 8,487,048 B2 | 7/2013 | Wada et al. |
| 8,519,041 B2 | 8/2013 | Smith et al. |
| 8,647,317 B2 | 2/2014 | Tian et al. |
| 8,653,210 B2 | 2/2014 | Fricker et al. |
| 8,653,320 B2 | 2/2014 | Furno et al. |
| 8,658,146 B2 | 2/2014 | Furno et al. |
| 8,686,216 B2 | 4/2014 | Wattebled et al. |
| 9,074,022 B2 | 7/2015 | Yokoyama et al. |
| 2002/0039869 A1 | 4/2002 | Achille |
| 2003/0118821 A1 | 6/2003 | Sun et al. |
| 2005/0137546 A1* | 6/2005 | Joy .................. A61L 15/60 604/368 |
| 2006/0182706 A1 | 8/2006 | Mathauer et al. |
| 2008/0215026 A1 | 9/2008 | Schornick et al. |
| 2008/0280128 A1 | 11/2008 | Furno et al. |
| 2009/0023006 A1 | 1/2009 | Bub et al. |
| 2009/0105389 A1 | 4/2009 | Walden et al. |
| 2009/0227741 A1 | 9/2009 | Walden et al. |
| 2010/0035757 A1 | 2/2010 | Furno et al. |
| 2010/0036004 A1 | 2/2010 | Harren et al. |
| 2010/0057027 A1 | 3/2010 | Furno et al. |
| 2011/0313113 A1 | 12/2011 | Sakamoto et al. |
| 2012/0001122 A1 | 1/2012 | Wattebled et al. |
| 2012/0258851 A1 | 10/2012 | Nakatsuru et al. |
| 2012/0267570 A1 | 10/2012 | Shi et al. |
| 2012/0271260 A1 | 10/2012 | Azad et al. |
| 2012/0302445 A1 | 11/2012 | Rudolph et al. |
| 2012/0309905 A1 | 12/2012 | Fricker et al. |
| 2013/0011601 A1 | 1/2013 | Fenske |
| 2013/0012899 A1 | 1/2013 | Fenske |
| 2013/0026412 A1 | 1/2013 | Machida et al. |
| 2013/0101851 A1 | 4/2013 | Takaai et al. |
| 2013/0253158 A1 | 9/2013 | Naumann et al. |
| 2014/0031498 A1 | 1/2014 | Smith et al. |
| 2014/0045683 A1 | 2/2014 | Loick et al. |
| 2014/0054497 A1 | 2/2014 | Wattebled et al. |

FOREIGN PATENT DOCUMENTS

| | | |
|---|---|---|
| DE | 2706135 A1 | 8/1978 |
| DE | 3503458 A1 | 8/1985 |
| DE | 4020780 C1 | 8/1991 |
| DE | 4323001 | 7/1993 |
| DE | 4244548 A1 | 7/1994 |
| DE | 4418818 A1 | 1/1995 |
| DE | 4333056 A1 | 3/1995 |
| DE | 102009049450 A1 | 6/2011 |
| EP | 170186 B1 | 9/1991 |
| EP | 0644207 A1 | 3/1995 |
| EP | 0826349 A2 | 3/1998 |
| EP | 1255857 A2 | 11/2002 |
| EP | 0827753 B1 | 8/2003 |
| EP | 0744435 B1 | 9/2003 |
| EP | 1493453 A1 | 1/2005 |
| EP | 1858998 B1 | 6/2010 |
| EP | 2399944 A1 | 12/2011 |
| EP | 2518092 A1 | 10/2012 |
| EP | 2566901 A1 | 3/2013 |
| JP | H11199602 A | 7/1999 |
| JP | 2006520832 | 9/2006 |
| JP | 2010506710 A | 3/2010 |
| JP | 2011510145 | 3/2011 |
| JP | 2013525592 A | 6/2013 |
| KR | 20090017543 A | 2/2009 |
| RU | 1777603 A3 | 11/1992 |
| RU | 2326892 C2 | 6/2008 |
| WO | 9511651 A1 | 5/1995 |
| WO | 9511652 A1 | 5/1995 |
| WO | 9511653 A1 | 5/1995 |
| WO | 9511654 A1 | 5/1995 |
| WO | 9617884 A1 | 6/1996 |
| WO | 9711659 A1 | 4/1997 |
| WO | 9837846 A1 | 9/1998 |
| WO | 9847454 A1 | 10/1998 |
| WO | 9934843 A1 | 7/1999 |
| WO | 0102609 A1 | 1/2001 |
| WO | 0115647 A1 | 3/2001 |
| WO | 0189439 A1 | 11/2001 |
| WO | 2004071363 A1 | 8/2004 |
| WO | 2004099265 A1 | 11/2004 |
| WO | 2008117109 A1 | 10/2008 |
| WO | 2008155699 A1 | 12/2008 |
| WO | 2008155701 A2 | 12/2008 |
| WO | 2008155702 A1 | 12/2008 |
| WO | 2008155710 A1 | 12/2008 |
| WO | 2008155711 A1 | 12/2008 |
| WO | 2008155722 A2 | 12/2008 |
| WO | 2010095427 A1 | 8/2010 |
| WO | 2011078298 A1 | 6/2011 |
| WO | 2011120504 A2 | 10/2011 |
| WO | 2011139883 A1 | 11/2011 |

OTHER PUBLICATIONS

Written Opinion of the International Searching Authority mailed on May 8, 2005 in PCT/US2004/04229 (8 pages).

Corrected version of Written Opinion (English) mailed on Jun. 24, 2014 in PCT/EP2012/072352 (6 pages).

English translation of International Search Report mailed on Jun. 10, 2014 in PCT/EP2012/072352 (2 pages).

Buchholz, Frederick L. and Graham, Andrew T., "Modern Superabsorbent Polymer Technology," copyright 1998, John Wiley & Sons, Inc., Chapter 1: "Absorbency and Superabsorbency," pp. 1-17 (19 pages).

Buchholz, Frederick L. and Graham, Andrew T., "Modern Superabsorbent Polymer Technology," copyright 1998, John Wiley

(56) References Cited

OTHER PUBLICATIONS

& Sons, Inc., Chapter 2: "Chemistry of Superabsorbent Polyacrylates," pp. 19-67 (51 pages).
Buchholz, Frederick L. and Graham, Andrew T., "Modern Superabsorbent Polymer Technology," copyright 1998, John Wiley & Sons, Inc., Chapter 3: "Commercial Processes for the Manufacture of Superabsorbent Polymers," pp. 69-117 (51 pages).
Buchholz, Frederick L. and Graham, Andrew T., "Modern Superabsorbent Polymer Technology," copyright 1998, John Wiley & Sons, Inc., Chapter 4: "Analysis and Characterization of Superabsorbent Polymers," pp. 119-165 (49 pages).
Buchholz, Frederick L. and Graham, Andrew T., "Modern Superabsorbent Polymer Technology," copyright 1998, John Wiley & Sons, Inc., Chapter 5: "The Structure and Properties of Superabsorbent Polyacrylates," pp. 167-221 (57 pages).

\* cited by examiner

SUPERABSORBING POLYMERS WITH RAPID ABSORPTION PROPERTIES AND METHOD FOR PRODUCING THE SAME

This application is a national stage application under 35 U.S.C. §371 of International Application No. PCT/EP2012/072352 filed 12 Nov. 2012, which claims priority to German Application No. DE 10 2011 086 516.0 filed 17 Nov. 2011, the disclosures of which are expressly incorporated herein by reference.

The present invention relates to superabsorbent polymers with rapid absorption properties and to processes for production thereof.

FIELD

The current trend in diaper construction is to produce even thinner constructions with reduced cellulose fiber content and increased superabsorbent content. The advantage of thinner constructions is exhibited not just in improved wear comfort but also in reduced costs in packaging and storage. With the trend toward ever thinner diaper constructions, the profile of requirements on the superabsorbents has changed significantly. Of crucial significance is now the ability of the hydrogel to conduct and distribute the liquid. Owing to the higher loading of the hygiene article (amount of superabsorbent per unit area), the polymer in the swollen state must not form a barrier layer for subsequent liquid (gel blocking). If the product has good transport properties, optimal exploitation of the overall hygiene article can be ensured.

BACKGROUND

In addition to the permeability of the superabsorbents (SAPs) (reported in the form of what is called the "Saline Flow Conductivity—SFC") and the absorption capacity under compressive stress, the absorption rate of the superabsorbent particles in particular (reported in amount of liquid absorbed per gram of superabsorbent per second) is also a crucial criterion which enables statements about whether an absorbent core which comprises this superabsorbent in a large concentration and has only a low fluff content is capable, on its first contact with liquids, of absorbing them rapidly (called "acquisition"). In the case of absorbent cores with a high superabsorbent content, this "acquisition" depends, among other factors, on the absorption rate of the superabsorbent material.

From the prior art, there are various known property rights which are supposed to enable an increase in the absorption rate of superabsorbent particles. WO96/17884A1 discloses a water-absorbing resin for which a solid blowing agent with a particle diameter of 1 to 100 µm is used in the monomer solution. In principle, preference is given to organic azo compounds and here specifically to the acrylic salts of azo compounds containing an amino group. Pure carbonates, ammonium nitride or mixtures thereof can optionally be used.

Disadvantages here are the rapid conversion of the azo compounds and the basic dispersion of the small solid particles in the monomer solution. Larger particles cannot be dispersed well without separation of particles and monomer solution in the dispersion before it reaches the gel point.

A disadvantage here in the case of use of superabsorbents known from the prior art is that leakage problems occur, since the SAP either absorbs the liquid too slowly and/or has unsuitable liquid transportation.

The current trend particularly in diaper construction is to produce even thinner absorbent cores with reduced cellulose fiber content and increased superabsorbent content. The advantage of thinner constructions is exhibited not just in improved wear comfort but also in reduced costs in packaging and storage. The newest generation of absorbent cores, which is described, for example, in WO-A-2008/155722, WO-A-2008/155711, WO-A-2008/155710, WO-A-2008/155702, WO-A-2008/155701, WO-A-2008/155699, EP-A-1 225 857, WO-A-01/15647, WO-A-2011/120504, DE-A-10 2009 049 450, WO-A-2008/117109, WO-A-97/11659, EP-A-0 826 349, WO-A-98/37846, WO-A-95/11653, WO-A-95/11651, WO-A-95/11652, WO-A-95/11654, WO-A-2004/071363 or WO-A-01/89439, is essentially cellulose-free (which is why corresponding diapers are also referred to as "flufless diapers"). The immobilization of the superabsorbent particles, which in cellulose-containing absorbent cores is effected by the cellulose fibers, can be achieved in this newest generation of absorbent cores by, for example, immobilizing the superabsorbent particles on a substrate surface by means of thermoplastic fibers.

With the trend toward ever thinner diaper constructions and the omission of the temporary liquid storage and conduction function of the cellulose fibers, the profile of requirements on the superabsorbents has changed significantly. A factor of crucial importance is now the ability of the hydrogel to prevent the leakage of urine directly on micturition. This is achieved by the property of the superabsorbent/hydrogel of effectively absorbing the liquid during swelling and distributing it in the gel layer, with simultaneous minimization of the amount of unbound urine in the diaper. Due to good transport properties, advantageous superabsorbents also lead to optimal exploitation of the overall hygiene article.

U.S. Pat. No. 5,154,713 discloses water-absorbing polymers which are prepared by means of a carbonate blowing agent in the monomer solution. The carbonate particles are introduced here into the monomer solution well before the actual polymerization, and the initiator is added from 5 to 15 minutes after the dispersion of the carbonate blowing agent, as a result of which homogeneous distribution of these carbonate particles is not ensured and a not inconsiderable portion of the carbonate may be discharged again.

EP0644207 discloses superabsorbent polymers which are likewise admixed with an organic carbonate blowing agent in the monomer solution. Disadvantages here are the use of amine compounds, and also the elimination products of the organic carbonates remaining in the superabsorbent.

WO 2010/095427 discloses water-absorbing polymers in which a gas is dispersed into the monomer solution. This gas is nitrogen, argon, helium, carbon dioxide or the like, which is intended to ensure a more porous structure. The intention is to maintain these microbubbles in the monomer solution by means of polyoxyethylene-(20) sorbitan monostearate until the polymerization sets in. A disadvantage here is that the surfactants can be washed out of the end product again and adversely affect performance.

A factor of crucial importance is now the ability of the hydrogel to prevent the leakage of urine directly on micturition. This is achieved by the property of the superabsorbent/hydrogel of effectively absorbing the liquid during swelling and distributing it in the gel layer, with simultaneous minimization of the amount of unbound urine in the diaper. Due to good transport properties, advantageous superabsorbents also lead to optimal exploitation of the overall hygiene article.

The term "rewet" is generally understood to mean the property of a superabsorbent or of a composite comprising a superabsorbent to release liquid to an absorptive ply under compressive stress. The term "absorptive ply" is understood to mean, for example, paper, filter paper, collagen, sponges, foams or the like.

EP1858998B1 discloses superabsorbent foams where the monomer solution gives rise to foam only under an elevated pressure of 12 bar by addition of carbon dioxide and surfactants. However, the superabsorbents known to date from the prior art are only of inadequate suitability for use in the above-described new generation of cellulose-free diaper constructions.

In general, it is an object of the present invention to overcome the disadvantages arising from the prior art.

More particularly, it is an object of the present invention to provide a process for producing a water-absorbing polymer which has an improved swell rate and faster absorption of liquids, while simultaneously maintaining the overall quality, and more particularly a high permeability.

It is also a further object to perform the process in an economically simple manner, the intention being to minimize the use of organic additives, and also a mode of operation at ambient pressure.

It is a particular object of the present invention to provide a process by which water-absorbing polymers can be produced, and a particularly high swell rate can be ensured.

It is a further object of the present invention, in addition, to provide a process by which it is possible to produce water-absorbing polymers which ensure rapid and active liquid transportation, for example in thin diapers, such that rapid absorption and good distribution, i.e. corresponding capillarity, are ensured.

It is a further object of the invention, in particular, to specify a water-absorbing polymer, composites comprising such water-absorbing polymers, and chemical products comprising such water-absorbing polymers or composites, the water-absorbing polymers having an increased absorption capacity for aqueous solutions.

SUMMARY

These objects are achieved by the subject-matter of the category-forming claims. Advantageous configurations and developments which can occur individually or in combination form the subject-matter of the dependent claims in each case.

A contribution to the achievement of the object stated at the outset is made by the process for producing a water-absorbing polymer, comprising the process steps of
(i) mixing
  ($\alpha$1) 0.1 to 99.999% by weight, preferably 20 to 98.99% by weight and more preferably 30 to 98.95% by weight of polymerizable, ethylenically unsaturated monomers containing acid groups, or salts thereof, or polymerizable, ethylenically unsaturated monomers including a protonated or quaternized nitrogen, or mixtures thereof, particular preference being given to mixtures including at least ethylenically unsaturated monomers containing acid groups, preferably acrylic acid,
  ($\alpha$2) 0 to 70% by weight, preferably 1 to 60% by weight and more preferably 1 to 40% by weight of polymerizable, ethylenically unsaturated monomers copolymerizable with ($\alpha$1),
  ($\alpha$3) 0.001 to 10% by weight, preferably 0.01 to 7% by weight and more preferably 0.05 to 5% by weight of one or more crosslinkers,
  ($\alpha$4) 0 to 30% by weight, preferably 1 to 20% by weight and more preferably 5 to 10% by weight of water-soluble polymers,
  ($\alpha$5) 0 to 20% by weight, preferably 0.01 to 7% by weight and more preferably 0.05 to 5% by weight of one or more assistants, where the sum of their weights ($\alpha$1) to ($\alpha$5) is 100% by weight,
(ii) free-radical polymerization with crosslinking to form a water-insoluble, aqueous untreated hydrogel polymer,
(iii) drying the hydrogel polymer,
(iv) grinding and sieving the hydrogel polymer to size,
(v) surface postcrosslinking the ground and sieved hydrogel polymer and
(vi) drying and finishing the water-absorbing polymer,
wherein
the aqueous monomer solution, prior to the addition of the initiator and the commencement of free-radical polymerization, is admixed with 0.01 to 5% by weight, preferably 0.02 to 2% by weight and more preferably 0.07 to 1% by weight of at least one surfactant from the group of the nonionic, ionic or amphoteric surfactants and optionally 0.01 to 5% by weight, preferably 0.02 to 2% by weight and more preferably 0.07 to 1% by weight of a blowing agent having a particle size of 10 μm to 900 μm, based on the water-absorbing polymer.

DETAILED DESCRIPTION

The term "water-absorbing polymer" is understood in accordance with the invention to mean the superabsorbent.

In a further embodiment, a hydrogel is, comprising the process steps of
(i) mixing
  ($\alpha$1) 0.1 to 99.999% by weight, preferably 20 to 98.99% by weight and more preferably 30 to 98.95% by weight of polymerizable, ethylenically unsaturated monomers containing acid groups, or salts thereof, or polymerizable, ethylenically unsaturated monomers including a protonated or quaternized nitrogen, or mixtures thereof, particular preference being given to mixtures including at least ethylenically unsaturated monomers containing acid groups, preferably acrylic acid,
  ($\alpha$2) 0 to 70% by weight, preferably 1 to 60% by weight and more preferably 1 to 40% by weight of polymerizable, ethylenically unsaturated monomers copolymerizable with ($\alpha$1),
  ($\alpha$3) 0.001 to 10% by weight, preferably 0.01 to 7% by weight and more preferably 0.05 to 5% by weight of one or more crosslinkers,
  ($\alpha$4) 0 to 30% by weight, preferably 1 to 20% by weight and more preferably 5 to 10% by weight of water-soluble polymers,
  ($\alpha$5) 0 to 20% by weight, preferably 0.01 to 7% by weight and more preferably 0.05 to 5% by weight of one or more assistants, where the sum of the weights of ($\alpha$1) to ($\alpha$5) is 100% by weight,
(ii) free-radical polymerization with crosslinking to form a water-insoluble, aqueous untreated hydrogel polymer,
(iii) drying the hydrogel polymer,
(iv) grinding and sieving the hydrogel polymer to size,
wherein
the aqueous monomer solution, prior to the addition of the initiator and the commencement of free-radical polymerization, is admixed with 0.01 to 5% by weight, preferably 0.02 to 2% by weight and more preferably 0.07 to 1% by weight of at least one surfactant from the group of the nonionic, ionic or amphoteric surfactants and optionally 0.01 to 5% by weight, preferably 0.02 to 2% by weight and more preferably 0.07 to 1% by weight of a blowing agent having a particle size of 10 μm to 900 μm, based on the hydrogel polymer.

This inventive hydrogel polymer can be converted by means of thermally induced postcrosslinking to an inventive water-absorbing polymer (superabsorbent).

Preference is given in accordance with the invention to ensuring that the surfactants are polymerized into the polymer network. Advantageously, this greatly lowers the amount of extractable surfactant constituents and, accordingly, only minimally reduces the surface tension.

According to the invention, the addition of surfactants and blowing agents to the monomer solution after polymerization achieves a fine porous gel structure and affords superabsorbent powders having a greater surface area. Advantageously, the inventive increase in the overall surface area ensures more rapid absorption of the liquid compared to conventional SAPs. This is shown by what is called the FSR value. The inventive water-absorbing polymers have an FSR in the range from 0.3 to 0.65, preferably 0.35 to 0.60. According to the invention, it is more preferable when the FSR value is greater than 0.40 g/g/s.

According to the invention, in spite of the use of the surfactants, there is no lowering in the surface tension values of the hydrogel polymers or superabsorbents.

According to the invention, the permeability, which is referred to as the SFC value (in the present invention always based on 1.5 g), of the water-absorbing polymer composition is in the range from 30 to 200, preferably 50 to 180 and more preferably in the range from 70 to 150.

According to the invention, the surface tension is in the range above 50 mN/m, preferably above 55 mN/m, more preferably above 60 mN/m and most preferably above 62 mN/m. According to the invention, the surface tension is not greater than 68 mN/m.

According to the invention, the particle size distribution PSD of the hydrogel polymer is such that more than 60% of the particles are in the range from 300 μm to 600 μm and less than 5% of the particles are smaller than 150 μm.

In the case of a low surface tension, this generally leads to increased rewet values, for example backsheet rewet, or to leakage for the diapers in which such superabsorbents are used. Advantageously, this problem is prevented by the process according to the invention, and in the form of the surfactants incorporable by polymerization. In addition, the superabsorbents exhibit comparable performance with regard to retention (CRC) and absorption against pressure (AAP).

Tailored surfactants are added to the monomer solution for the production of the inventive superabsorbents. These specific surfactants contain functional groups which are polymerizable. Preferred chemical structures are:

$R^1$-(EO)$_n$-block-(PO)$_m$—$R^2$ $R^1$ or $R^2$=methyl, ethyl, n-propyl, isopropyl, n-butyl, isobutyl, n-pentyl, 2-methylbutyl, 2,2-dimethylpropyl, —OH, acetyl or allyl, and n=2 to 20 and m=2 to 20.

EO and PO are respectively hydrophilic and hydrophobic blocks for generating surfactant properties. Reactive allyl groups are preferred since they, in accordance with the invention, are incorporated by polymerization later than acrylic groups and are more stable in the hydrolysis.

It is more preferable when 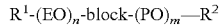 is an allyl radical and the other radical is an acetyl or —OH radical.

In the context of the present invention, the term "EO" is understood to mean an ether which is formed by polyaddition of ethylene oxide and is referred to as polyether or polyethylene glycol. In the present application, the term "allyl-(EO)$_n$-" refers to a group of the formula CH2=CH—CH2-O—(CH2-CH2-O)n-. In particular, it refers to compounds in which n is an integer from 2 to 20.

Preference is given to compounds in which n is 4 to 12 and more preferably n is 5 to 8.

In the context of the present invention, the term "PO" is in principle understood to mean propylene oxide according to the formula —(CH$_2$—CH(CH$_3$)—O)$_m$. In this formula, m is an integer from 2 to 20. Preference is given to compounds in which m is 3 to 12 and more preferably m is 4 to 7.

Preferably, for the distribution of the two different blocks, 2≤m≤n≤20, such that a hydrophilic base structure is ensured and the surfactant has a defined water solubility.

Preference is given to surfactants of the following formula:

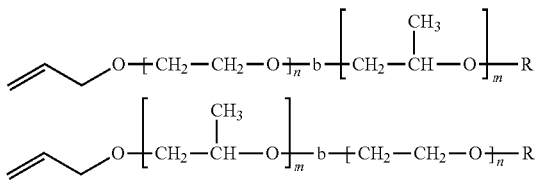

In this formula, R corresponds to $R^1$ or $R^2$.

In the context of the present invention, the individual PO units may be isotactic, syndiotactic or atactic sequences of the configuration in the molecule.

The blowing agents used may be all carbonates from the group of lithium carbonate, sodium carbonate, potassium carbonate, rubidium carbonate, caesium carbonate, or higher-valency metal ions such as beryllium carbonate, calcium carbonate, magnesium carbonate, strontium carbonate or mixtures thereof. Further compounds used may also be granulated carbonates, which are also produced as mixed salts of a carbonate and/or percarbonate with a further salt which functions as an outer layer, for example a sulphate compound. According to the invention, the blowing agents have a particle size of 10 μm to 900 μm, preferably 50 μm to 500 μm and more preferably 100 μm to 450 μm.

According to the invention, the surfactants are generally used simultaneously with the crosslinker. In one embodiment, the blowing agent is added after the addition of the surfactant. In further embodiments, the blowing agent can be supplied at the same time as or before the surfactant.

On addition of blowing agents or sodium carbonate, small bubbles form, these having a smaller diameter in the presence of surfactants.

According to the invention, the surfactants stabilize the large gas surface area which arises in the solution through the blowing agent. The polymerization which proceeds in parallel fixes a fine porous structure (porous gel). The surfactants are "inactivated" during the polymerization, which means that they can be incorporated in the polymer network or are incorporated due to their reactive functionality.

The synergy observed between surfactants and blowing agents advantageously allows the use of smaller amounts of blowing agent, for example carbonate. Typical disadvantages associated with carbonates include the possible difficulties in the mixing and addition in the solution, and uncontrolled dispersion of the small bubbles formed, for example significant coalescence or excessively large bubbles, or the loss of other properties of the SAP.

The monoethylenically unsaturated monomers ($\alpha$1) containing acid groups may be partly or fully neutralized, preferably partly. The monoethylenically unsaturated monomers containing acid groups have preferably been neutralized to an extent of at least 10 mol %, more preferably to an extent of at least 25 to 50 mol % and further preferably to an extent of 50 to 90 mol %. The neutralization of the monomers ($\alpha$1) may precede or else follow the polymerization. In this case, the partial neutralization is effected to an extent of at least 10 mol %, more preferably to an extent of at least 25 to 50 mol % and further preferably to an extent of 50 to 90 mol %. Moreover, neutralization can be effected with alkali metal hydroxides, alkaline earth metal hydroxides, ammonia, and carbonates and bicarbonates. In addition, any further base which forms a water-soluble salt with the acid is conceivable. Mixed neutralization with different bases is also conceivable. Preference is given to neutralization with ammonia or with alkali metal hydroxides, more preferably with sodium hydroxide or with ammonia.

In addition, the free acid groups in a polymer may predominate, such that this polymer has a pH within the acidic range. This acidic water-absorbing polymer may be at least partly neutralized by a polymer with free basic groups, preferably amine groups, which is basic compared to the acid polymer. These polymers are referred to in the literature as "Mixed-Bed Ion-Exchange Absorbent Polymers" (MBIEA polymers) and are disclosed in WO 99/34843 inter alia. The disclosure of WO 99/34843 is hereby incorporated by reference and is thus considered to form part of the disclosure. In general, MBIEA polymers constitute a composition which includes firstly basic polymers capable of exchanging anions, and secondly a polymer which is acidic compared to the basic polymer and is capable of exchanging cations. The basic polymer has basic groups and is typically obtained by the polymerization of monomers which bear basic groups or groups which can be converted to basic groups. These monomers are in particular those which have primary, secondary or tertiary amines or the corresponding phosphines, or at least two of the above functional groups. This group of monomers includes especially ethyleneamine, allylamine, diallylamine, 4-aminobutene, alkyloxycyclines, vinylformamide, 5-aminopentene, carbodiimide, formaldacine, melamine and the like, and the secondary or tertiary amine derivatives thereof.

Preferred monoethylenically unsaturated monomers ($\alpha$1) containing acid groups are acrylic acid, methacrylic acid, ethacrylic acid, $\alpha$-chloroacrylic acid, $\alpha$-cyanoacrylic acid, $\beta$-methylacrylic acid (crotonic acid), $\alpha$-phenylacrylic acid, $\beta$-acryloyloxypropionoic acid, sorbic acid, $\alpha$-chlorosorbic acid, 2'-methylisocrotonic acid, cinnamic acid, p-chlorocinnamic acid, $\beta$-stearyl acid, itaconic acid, citraconic acid, mesaconic acid, glutaconic acid, aconitic acid, maleic acid, fumaric acid, tricarboxyethylene and maleic anhydride, preference being given particularly to acrylic acid and methacrylic acid and additionally to acrylic acid.

In addition to these monomers containing carboxylate groups, preferred monoethylenically unsaturated monomers ($\alpha$1) containing acid groups additionally include ethylenically unsaturated sulphonic acid monomers or ethylenically unsaturated phosphonic acid monomers.

Preferred ethylenically unsaturated sulphonic acid monomers are allylsulphonic acid or aliphatic or aromatic vinylsulphonic acids or acrylic or methacrylic sulphonic acids. Preferred aliphatic or aromatic vinylsulphonic acids are vinylsulphonic acid, 4-vinylbenzylsulphonic acid, vinyltoluenesulphonic acid and styrenesulphonic acid. Preferred acryloyl- or methacryloylsulphonic acids are sulphoethyl (meth)acrylate, sulphopropyl (meth)acrylate, 2-hydroxy-3-methacryloyloxypropylsulphonic acid, and (meth)acrylamidoalkylsulphonic acids such as 2-acrylamido-2-methylpropanesulphonic acid.

Preferred ethylenically unsaturated phosphonic acid monomers are vinylphosphonic acid, allylphosphonic acid, vinylbenzylphosphonic acid, (meth)acrylamidoalkylphosphonic acids, acrylamidoalkyldiphosphonic acids, phosphonomethylated vinylamines and (meth)acryloylphosphonic acid derivatives.

Preferred ethylenically unsaturated monomers ($\alpha$1) containing a protonated nitrogen are preferably dialkylaminoalkyl (meth)acrylates in protonated form, for example dimethylaminoethyl (meth)acrylate hydrochloride or dimethylaminoethyl (meth)acrylate hydrosulphate, and dialkylaminoalkyl(meth)acrylamides in protonated form, for example dimethylaminoethyl(meth)acrylamide hydrochloride, dimethylaminopropyl(meth)acrylamide hydrochloride, dimethylaminopropyl(meth)acrylamide hydrosulphate or dimethylaminoethyl-(meth)acrylamide hydrosulphate.

Preferred ethylenically unsaturated monomers ($\alpha$1) containing a quaternized nitrogen are dialkylammonioalkyl (meth)acrylates in quaternized form, for example trimethylammonioethyl (meth)acrylate methosulphate or dimethylethylammonioethyl (meth)acrylate etho-sulphate, and (meth)acrylamidoalkyldialkylamines in quaternized form, for example (meth)acrylamidopropyltrimethylammonium chloride, trimethylammonioethyl (meth)acrylate chloride or (meth)acrylamidopropyltrimethylammonium sulphate.

Preferred monoethylenically unsaturated monomers ($\alpha$2) copolymerizable with ($\alpha$1) are acrylamides and methacrylamides.

Preferred (meth)acrylamides are, in addition to acrylamide and methacrylamide, alkyl-substituted (meth)acrylamides or aminoalkyl-substituted derivatives of (meth)acrylamide, such as N-methylol(meth)acrylamide, N,N-dimethylamino(meth)acrylamide, dimethyl(meth)acrylamide or diethyl(meth)acrylamide. Possible vinylamides are, for example, N-vinylamides, N-vinylformamides, N-vinylacetamides, N-vinyl-N-methylacetamides, N-vinyl-N-methylformamides, vinylpyrrolidone. Among these monomers, particular preference is given to acrylamide.

Additionally preferred as monoethylenically unsaturated monomers ($\alpha$2) copolymerizable with ($\alpha$1) are water-dispersible monomers. Preferred water-dispersible monomers are acrylic esters and methacrylic esters, such as methyl (meth)acrylate, ethyl (meth)acrylate, propyl (meth)acrylate or butyl (meth)acrylate, and also vinyl acetate, styrene and isobutylene.

Crosslinkers ($\alpha$3) preferred in accordance with the invention are compounds having at least two ethylenically unsaturated groups within one molecule (crosslinker class I), compounds having at least two functional groups which can react with functional groups of monomers ($\alpha$1) or ($\alpha$2) in a condensation reaction (=condensation crosslinkers), in an addition reaction or in a ring-opening reaction (crosslinker class II), compounds which have at least one ethylenically unsaturated group and at least one functional group which can react with functional groups of monomers ($\alpha$1) or ($\alpha$2) in a condensation reaction, in an addition reaction or in a ring-opening reaction (crosslinker class III), or polyvalent metal cations (crosslinker class IV). The compounds of crosslinker class I achieve crosslinking of the polymers through the free-radical polymerization of the ethylenically unsaturated groups of the crosslinker molecule with the monoethylenically unsaturated monomers ($\alpha 1$) or ($\alpha 2$), while the compounds of the crosslinker class II and the polyvalent metal cations of crosslinker class IV achieve crosslinking of the polymers by a condensation reaction of the functional groups (crosslinker class II) or by electrostatic interaction of the polyvalent metal cation (crosslinker class IV) with the functional groups of monomers ($\alpha 1$) or ($\alpha 2$). In the case of the compounds of crosslinker class III, there is correspondingly crosslinking of the polymer both by free-radical polymerization of the ethylenically unsaturated group and by a condensation reaction between the functional group of the crosslinker and the functional groups of monomers ($\alpha 1$) or ($\alpha 2$).

Preferred compounds of crosslinker class I are poly(meth) acrylic esters which are obtained, for example, by the reaction of a polyol, for example ethylene glycol, propylene glycol, trimethylolpropane, 1,6-hexanediol, glycerol, pentaerythritol, polyethylene glycol or polypropylene glycol, of an amino alcohol, of a polyalkylenepolyamine, for example diethylenetriamine or triethylenetetramine, or of an alkoxylated polyol with acrylic acid or methacrylic acid. Preferred compounds of crosslinker class I are additionally polyvinyl to compounds, poly(meth)allyl compounds, (meth)acrylic esters of a monovinyl compound or (meth)acrylic esters of a mono(meth)allyl compound, preferably of the mono(meth) allyl compounds of a polyol or of an amino alcohol. In this context, reference is made to DE 195 43 366 and DE 195 43 368. The disclosures are hereby incorporated by reference and are thus considered to form part of the disclosure.

Examples of compounds of crosslinker class I include alkenyl di(meth)acrylates, for example ethylene glycol di(meth)acrylate, 1,3-propylene glycol di(meth)acrylate, 1,4-butylene glycol di(meth)acrylate, 1,3-butylene glycol di(meth)acrylate, 1,6-hexanediol di(meth)acrylate, 1,10-decanediol di(meth)acrylate, 1,12-dodecanediol di(meth)acrylate, 1,18-octadecanediol di(meth)acrylate, cyclopentanediol di(meth)acrylate, neopentyl glycol di(meth) acrylate, methylene di(meth)acrylate or pentaerythritol di(meth)acrylate, alkenyldi(meth)acrylamides, for example N-methyldi(meth)acrylamide, N,N'-3-methylbutylidenebis (meth)acrylamide, N,N'-(1,2-dihydroxyethylene)bis(meth) acrylamide, N,N'-hexamethylenebis(meth)acrylacrylamide or N,N'-methylenebis(meth)acrylamide, polyalkoxy di(meth)acrylates, for example diethylene glycol di(meth)acrylate, triethylene glycol di(meth)acrylate, tetraethylene glycol di(meth)acrylate, dipropylene glycol di(meth)acrylate, tripropylene glycol di(meth)acrylate or tetrapropylene glycol di(meth)acrylate, bisphenol A di(meth)acrylate, ethoxylated bisphenol A di(meth)acrylate, benzylidene di(meth) acrylate, 1,3-di(meth)acryloyloxy-2-propanol, hydroquinone di(meth)acrylate, di(meth)acrylate esters of trimethylolpropane which has preferably been alkoxylated, preferably ethoxylated, with 1 to 30 mol of alkylene oxide per hydroxyl group, thioethylene glycol di(meth)acrylate, thiopropylene glycol di(meth)acrylate, thiopolyethylene glycol di(meth)acrylate, thiopolypropylene glycol di(meth) acrylate, divinyl ethers, for example 1,4-butanediol divinyl ether, divinyl esters, for example divinyl adipate, alkadienes, for example butadiene or 1,6-hexadiene, divinylbenzene, di(meth)allyl compounds, for example di(meth)allyl phthalate or di(meth)allyl succinate, homo- and copolymers of di(meth)allyldimethylammonium chloride and homo- and copolymers of diethyl(meth)allylaminomethyl (meth)acrylate ammonium chloride, vinyl (meth)acryloyl compounds, for example vinyl (meth)acrylate, (meth)allyl (meth)acryloyl compounds, for example (meth)allyl (meth)acrylate, (meth)allyl (meth)acrylate ethoxylated with 1 to 30 mol of ethylene oxide per hydroxyl group, di(meth)allyl esters of polycarboxylic acids, for example di(meth)allyl maleate, di(meth)allyl fumarate, di(meth)allyl succinate or di(meth) allyl terephthalate, compounds having 3 or more ethylenically unsaturated, free-radically polymerizable groups, for example glyceryl tri(meth)acrylate, (meth)acrylate esters of glycerol which has been ethoxylated with preferably 1 to 30 mol of ethylene oxide per hydroxyl group, trimethylolpropane tri(meth)acrylate, tri(meth)acrylate esters of trimethylolpropane which has preferably been alkoxylated, preferably ethoxylated, with 1 to 30 mol of alkylene oxide per hydroxyl group, trimethacrylamide, (meth)allylidene di(meth)acrylate, 3-allyloxy-1,2-propanediol di(meth)acrylate, tri(meth) allyl cyanurate, tri(meth)allyl isocyanurate, pentaerythritol tetra(meth)acrylate, pentaerythritol tri(meth)acrylate, (meth) acrylic esters of pentaerythritol ethoxylated with preferably 1 to 30 mol of ethylene oxide per hydroxyl group, tris(2-hydroxyethyl) isocyanurate tri(meth)acrylate, trivinyl trimellitate, tri(meth)allylamine, di(meth)allylalkylamines, for example di(meth)allylmethylamine, tri(meth)allyl phosphate, tetra(meth)allylethylenediamine, poly(meth)allyl esters, tetra(meth)allyloxyethane or tetra(meth)allylammonium halides.

Preferred compounds of crosslinker class II are compounds which have at least two functional groups which can react in a condensation reaction (=condensation crosslinkers), in an addition reaction or in a ring-opening reaction with the functional groups of monomers ($\alpha 1$) or ($\alpha 2$), preferably with acid groups of monomers ($\alpha 1$). These functional groups of the compounds of crosslinker class II are preferably alcohol, amine, aldehyde, glycidyl, isocyanate, carbonate or epichloro functions.

Examples of compounds of crosslinker class II include polyols, for example ethylene glycol, polyethylene glycols such as diethylene glycol, triethylene glycol and tetraethylene glycol, propylene glycol, polypropylene glycols such as dipropylene glycol, tripropylene glycol or tetrapropylene glycol, 1,3-butanediol, 1,4-butanediol, 1,5-pentanediol, 2,4-pentanediol, 1,6-hexanediol, 2,5-hexanediol, glycerol, polyglycerol, trimethylolpropane, polyoxypropylene, oxyethylene-oxypropylene block copolymers, sorbitan fatty acid esters, polyoxyethylenesorbitan fatty acid esters, pentaerythritol, polyvinyl alcohol and sorbitol, amino alcohols, for example ethanolamine, diethanolamine, triethanolamine or propanolamine, polyamine compounds, for example ethylenediamine, diethylenetriamine, triethylenetetramine, tetraethylenepentamine or pentaethylenehexamine, polyglycidyl ether compounds such as ethylene glycol diglycidyl ether, polyethylene glycol diglycidyl ether, glyceryl diglycidyl ether, glyceryl polyglycidyl ether, pentaerythrityl polyglycidyl ether, propylene glycol diglycidyl ether, polypropylene glycol diglycidyl ether, neopentyl glycol diglycidyl ether, hexanediol glycidyl ether, trimethylolpropane polyglycidyl ether, sorbitol polyglycidyl ether, diglycidyl phthalate, diglycidyl adipate, 1,4-phenylenebis(2-oxazoline), glycidol, polyisocyanates, preferably diisocyanates such as toluene 2,4-diisocyanate and hexamethylene diisocyanate, polyaziridine compounds such as 2,2-bishydroxymethylbutanol tris[3-(1-aziridinyl)propionate], 1,6-hexamethylenediethyleneurea and diphenylmethanebis-4,4'-N,N'-diethyleneurea, halogen peroxides, for example epichloro- and epibromohydrin and $\alpha$-methylepichlorohydrin, alkylene carbonates such as 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, 1,3-dioxolan-2-one, poly-1,3-dioxolan-2-one, polyquaternary amines such as condensation products of dimethylamines and epichlorohydrin. Preferred compounds of crosslinker class II are additionally polyoxazolines such as 1,2-ethylenebisoxazoline, crosslinkers with silane groups, such as γ-glycidoxypropyltrimethoxysilane and γ-aminopropyltrimethoxysilane, oxazolidinones such as 2-oxazolidinone, bis- and poly-2-oxazolidinones and diglycol silicates.

Preferred compounds of class III include hydroxyl- or amino-containing esters of (meth)acrylic acid, for example 2-hydroxyethyl (meth)acrylate and 2-hydroxypropyl(meth)acrylate, and also hydroxyl- or amino-containing (meth)acrylamides or mono(meth)allyl compounds of diols.

The polyvalent metal cations of crosslinker class IV derive preferably from mono- or polyvalent cations, the monovalent especially from alkali metals such as potassium, sodium, lithium, preference being given to lithium. Preferred divalent cations derive from zinc, beryllium, alkaline earth metals such as magnesium, calcium, strontium, preference being given to magnesium. Further higher-valency cations usable in accordance with the invention are cations of aluminum, iron, chromium, manganese, titanium, zirconium and other transition metals, and also double salts of such cations or mixtures of the salts mentioned. Preference is given to using aluminum salts and alums and the different hydrates thereof, for example $AlCl_3 \times 6H_2O$, $NaAl(SO_4)_2 \times 12 H_2O$, $KAl(SO_4)_2 \times 12 H_2O$ or $Al_2(SO_4)_3 \times 14\text{-}18H_2O$. Particular preference is given to using $Al_2(SO_4)_3$ and hydrates thereof as crosslinkers of crosslinking class IV.

The superabsorbent particles used in the process according to the invention are preferably crosslinked by crosslinkers of the following crosslinker classes, or by crosslinkers of the following combinations of crosslinker classes: I, II, III, IV, I II, I III, I IV, II III, I II IV, I III IV, II III IV, II IV or III IV. The above combinations of crosslinker classes are each a preferred embodiment of crosslinkers of a superabsorbent particle used in the process according to the invention.

Further preferred embodiments of the superabsorbent particles used in the process according to the invention are polymers which are crosslinked by any of the aforementioned crosslinkers of crosslinker class I. Among these, preference is given to water-soluble crosslinkers. In this context, particular preference is given to N,N'-methylenebisacrylamide, polyethylene glycol di(meth)acrylates, triallylmethylammonium chloride, tetraallylammonium chloride, and allyl nonaethylene glycol acrylate prepared with 9 mol of ethylene oxide per mole of acrylic acid.

As water-soluble polymers (α4), the superabsorbent particles may comprise water-soluble polymers, such as partly or fully hydrolyzed polyvinyl alcohol, polyvinylpyrrolidone, starch or starch derivatives, polyglycols or polyacrylic acid, preferably incorporated in polymerized form. The molecular weight of these polymers is uncritical provided that they are water-soluble. Preferred water-soluble polymers are starch or starch derivatives or polyvinyl alcohol. The water-soluble polymers, preferably synthetic water-soluble polymers such as polyvinyl alcohol, can also serve as a graft base for the monomers to be polymerized.

The assistants (α5) present in the polymers are organic or inorganic particles, for example odor binders, especially zeolites or cyclodextrins, skincare substances, surfactants or antioxidants.

The preferred organic assistants include cyclodextrins or derivatives thereof, and polysaccharides. Also preferred are cellulose and cellulose derivatives such as CMC, cellulose ethers. Preferred cyclodextrins or cyclodextrin derivatives are those compounds disclosed in DE-A-198 25 486 at page 3 line 51 to page 4 line 61. The aforementioned section of this published patent application is hereby incorporated by reference and is considered to form part of the disclosure of the present invention. Particularly preferred cyclodextrins are underivatized α-, β-, γ- or δ-cyclodextrins.

The inorganic particulate assistants used may be any materials which are typically used to modify the properties of water-absorbing polymers. The preferred inorganic assistants include sulphates such as $Na_2SO_4$, lactates, for instance sodium lactate, silicates, especially framework silicates such as zeolites, or silicates which have been obtained by drying aqueous silica solutions or silica sols, for example the commercially available products such as precipitated silicas and fumed silicas, for example Aerosils having a particle size in the range from 5 to 50 nm, preferably in the range from 8 to 20 nm, such as "Aerosil 200" from Evonik Industries AG, aluminates, titanium dioxides, zinc oxides, clay materials, and further minerals familiar to those skilled in the art, and also carbonaceous inorganic materials.

Preferred silicates are all natural or synthetic silicates which are disclosed as silicates in Hollemann and Wiberg, Lehrbuch der Anorganischen Chemie [Inorganic Chemistry], Walter de Gruyter-Verlag, 91st-100th edition, 1985, on pages 750 to 783. The aforementioned section of this textbook is hereby incorporated by reference and is considered to form part of the disclosure of the present invention.

Particularly preferred silicates are the zeolites. The zeolites used may be all synthetic or natural zeolites known to those skilled in the art. Preferred natural zeolites are zeolites from the natrolite group, the harmotone group, the mordenite group, the chabasite group, the faujasite group (sodalite group) or the analcite group. Examples of natural zeolites are analcime, leucite, pollucite, wairakite, bellbergite, bikitaite, boggsite, brewsterite, chabazite, willhendersonite, cowlesite, dachiardite, edingtonite, epistilbite, erionite, faujasite, ferrierite, amicite, garronite, gismondine, gobbinsite, gmelinite, gonnardite, goosecreekite, harmotone, phillipsite, wellsite, clinoptilolite, heulandite, laumontite, levyne, mazzite, merlinoite, montesommaite, mordenite, mesolite, natrolite, scolecite, offretite, paranatrolite, paulingite, perlialite, barrerite, stilbite, stellerite, thomsonite, tschernichite or yugawaralite. Preferred synthetic zeolites are zeolite A, zeolite X, zeolite Y, zeolite P, or the product ABSCENTS®.

The zeolites used may be zeolites of what is called the "intermediate" type, in which the $SiO_2/AlO_2$ ratio is less than 10; the $SiO_2/AlO_2$ ratio of these zeolites is more preferably within a range from 2 to 10. In addition to these "intermediate" zeolites, it is also possible to use zeolites of the "high" type, which include, for example, the known "molecular sieve" zeolites of the ZSM type, and β-zeolite. These "high" zeolites are preferably characterized by an $SiO_2/AlO_2$ ratio of at least 35, more preferably by an $SiO_2/AlO_2$ ratio within a range from 200 to 500.

The aluminates used are preferably the naturally occurring spinels, especially common spinel, zinc spinel, iron spinel or chromium spinel.

Preferred titanium dioxide is pure titanium dioxide in the rutile, anatase and brookite crystal forms, and also iron-containing titanium dioxides, for example ilmenite, calcium-containing titanium dioxides such as titanite or perovskite.

Preferred clay materials are those disclosed as clay materials in Hollemann and Wiberg, Lehrbuch der Anorganischen Chemie, Walter de Gruyter-Verlag, 91st-100th edition, 1985, on pages 783 to 785. Particularly the aforementioned section of this textbook is hereby incorporated by reference and is considered to form part of the disclosure of the present invention. Particularly preferred clay materials are kaolinite, illite, halloysite, montmorillonite and talc.

Further inorganic fines preferred in accordance with the invention are the metal salts of the mono-, oligo- and polyphosphoric acids. Among these, preference is given especially to the hydrates, particular preference being given to the mono- to decahydrates and trihydrates. Useful metals include especially alkali metals and alkaline earth metals, preference being given to the alkaline earth metals. Among these, Mg and Ca are preferred and Mg is particularly preferred. In the context of phosphates, phosphoric acids and metal compounds thereof, reference is made to Hollemann and Wiberg, Lehrbuch der Anorganischen Chemie, Walter de Gruyter-Verlag, 91st-100th edition, 1985, on pages 651 to 669. The aforementioned section of this textbook is hereby incorporated by reference and is considered to form part of the disclosure of the present invention.

Preferred carbonaceous but nonorganic assistants are those pure carbons which are mentioned as graphites in Hollemann and Wiberg, Lehrbuch der Anorganischen Chemie, Walter de Gruyter-Verlag, 91st-100th edition, 1985, on pages 705 to 708. The aforementioned section of this textbook is hereby incorporated by reference and is considered to form part of the disclosure of the present invention. Particularly preferred graphites are synthetic graphites, for example coke, pyrographite, activated carbon or carbon black.

The water-absorbing polymers obtained in the process according to the invention are preferably obtainable by first preparing a hydrogel polymer (PC) in particulate form from the aforementioned monomers and crosslinkers. This starting material for the water-absorbing polymers is produced, for example, by bulk polymerization which is preferably effected in kneading reactors such as extruders, solution polymerization, spray polymerization, inverse emulsion polymerization or inverse suspension polymerization. Preference is given to performing the solution polymerization in water as a solvent. The solution polymerization can be effected continuously or batchwise. The prior art discloses a wide spectrum of possible variations with regard to reaction conditions, such as temperatures, type and amount of the initiators, and of the reaction solution. Typical processes are described in the following patents: U.S. Pat. No. 4,286,082, DE 27 06 135, U.S. Pat. No. 4,076,663, DE 35 03 458, DE 40 20 780, DE 42 44 548, DE 43 23 001, DE 43 33 056, DE 44 18 818. The disclosures are hereby incorporated by reference and are thus considered to form part of the disclosure.

The initiators used to initiate the polymerization may be all initiators which form free radicals under the polymerization conditions and are typically used in the production of superabsorbents. These include thermal initiators, redox initiators and photoinitiators, which are activated by means of high-energy radiation. The polymerization initiators may be present dissolved or dispersed in a solution of inventive monomers. Preference is given to the use of water-soluble initiators.

Useful thermal initiators include all compounds which decompose to free radicals when heated and are known to those skilled in the art. Particular preference is given to thermal polymerization initiators having a half-life of less than 10 seconds, further preferably of less than 5 seconds at less than 180° C., further preferably at less than 140° C. Peroxides, hydroperoxides, hydrogen peroxide, persulphates and azo compounds are particularly preferred thermal polymerization initiators. In some cases, it is advantageous to use mixtures of different thermal polymerization initiators. Among these mixtures, preference is given to those of hydrogen peroxide and sodium peroxodisulphate or potassium peroxodisulphate, which can be used in any conceivable ratio. Suitable organic peroxides are preferably acetylacetone peroxide, methyl ethyl ketone peroxide, benzoyl peroxide, lauroyl peroxide, acetyl peroxide, capryl peroxide, isopropyl peroxydicarbonate, 2-ethylhexyl peroxydicarbonate, t-butyl hydroperoxide, cumene hydroperoxide, t-amyl perpivalate, t-butyl perpivalate, t-butyl perneohexanoate, t-butyl isobutyrate, t-butyl per-2-ethylhexanoate, t-butyl perisononanoate, t-butyl permaleate, t-butyl perbenzoate, t-butyl 3,5,5-trimethylhexanoate and amyl perneodecanoate. Further preferred thermal polymerization initiators are: azo compounds such as azobisisobutyronitrile, azobisdimethylvaleronitrile, 2,2'-azobis(2-amidinopropane)dihydrochloride, azobisamidinopropane dihydrochloride, 2,2'-azobis(N, N-dimethylene)isobutyramidine dihydrochloride, 2-(carbamoylazo)isobutyronitrile and 4,4'-azobis(4-cyanovaleric acid). The compounds mentioned are used in customary amounts, preferably within a range from 0.01 to 5 mol %, preferably from 0.1 to 2 mol %, based in each case on the amount of the monomers to be polymerized.

The redox initiators comprise, as the oxidic component, at least one of the above-specified per compounds, and, as the reducing component, preferably ascorbic acid, glucose, sorbose, mannose, ammonium hydrogensulphite, sulphate, thiosulphate, hyposulphite or sulphide, alkali metal hydrogensulphite, sulphate, thiosulphate, hyposulphite or sulphide, metal salts such as iron(II) ions or silver ions, or sodium hydroxymethylsulphoxylate. The reducing component used in the redox initiator is preferably ascorbic acid or sodium pyrosulphite. Based on the amount of monomers used in the polymerization, $1 \times 10^{-5}$ to 1 mol % of the reducing component of the redox initiator and $1 \times 10^{-5}$ to 5 mol % of the oxidizing component of the redox initiator are used. Instead of the oxidizing component of the redox initiator, or in addition thereto, it is possible to use one or more, preferably water-soluble, azo compounds.

If the polymerization is triggered by the action of high-energy radiation, it is customary to use what are called photoinitiators as the initiator. These may be, for example, what are called α-splitters, H-abstracting systems, or else azides. Examples of such initiators are benzophenone derivatives such as Michler's ketone, phenanthrene derivatives, fluorine derivatives, anthraquinone derivatives, thioxanthone derivatives, coumarin derivatives, benzoin ethers and derivatives thereof, azo compounds such as the above-mentioned free-radical initiators, substituted hexaarylbisimidazoles or acylphosphine oxides. Examples of azides are: 2-(N,N-dimethylamino)ethyl 4-azidocinnamate, 2-(N, N-dimethylamino)ethyl 4-azidonaphthyl ketone, 2-(N,N-dimethylamino)ethyl 4-azidobenzoate, 5-azido-1-naphthyl 2'-(N,N-dimethylamino)ethyl sulphone, N-(4-sulphonylazidophenyl)maleimide, N-acetyl-4-sulphonylazidoaniline, 4-sulphonylazidoaniline, 4-azidoaniline, 4-azidophenacyl bromide, p-azidobenzoic acid, 2,6-bis(p-azidobenzylidene)cyclohexanone and 2,6-bis (p-azido-benzylidene)-4-methylcyclohexanone. If they are used, the photoinitiators are employed typically in amounts of 0.01 to 5% by weight, based on the monomers to be polymerized.

Preference is given in accordance with the invention to using an initiator system consisting of hydrogen peroxide, sodium peroxodisulphate and ascorbic acid. In general, the polymerization is initiated with the initiators within a temperature range from 0° C. to 90° C.

The polymerization reaction can be triggered by one initiator or by a plurality of interacting initiators. In addition, the polymerization can be performed in such a way that one or more redox initiators are first added. Later in the polymerization, thermal initiators or photoinitiators are then applied additionally, and the polymerization reaction in the case of photoinitiators is then initiated by the action of high-energy radiation. The reverse sequence, i.e. the initial initiation of the reaction by means of high-energy radiation and photoinitiators or thermal initiators and initiation of the polymerization by means of one or more redox initiators later in the polymerization, is also conceivable.

In order to convert the hydrogel polymers (PC) thus obtained to a particulate form, they can first, after they have been removed from the reaction mixture, be dried at a temperature within a range from 20 to 300° C., preferably within a range from 50 to 250° C. and more preferably within a range from 100 to 200° C., down to a water content of less than 40% by weight, preferably of less than 20% by weight and further preferably of less than 10% by weight, based in each case on the total weight of the hydrogel polymer (PC). The drying is effected preferably in ovens or driers known to those skilled in the art, for example in belt driers, staged driers, rotary tube ovens, fluidized bed driers, pan driers, paddle driers or infrared driers.

According to the present invention, the comminution is preferably effected by dry grinding, preferably by dry grinding in a hammer mill, a pinned disc mill, a ball mill or a roll mill. In a further version of the present invention, the hydrogel polymer can also be comminuted by the combinations of two or more of the above-described mills.

In a preferred embodiment of the processes according to the invention, the water-absorbing polymers obtained are particles having an inner region and a surface region bordering the inner region. The surface region has a different chemical composition from the inner region, or differs from the inner region in a physical property. Physical properties in which the inner region differs from the surface region are, for example, the charge density or the degree of crosslinking.

These water-absorbing polymers having an inner region and a surface region bordering the inner region are preferably obtainable by postcrosslinking reactive groups close to the surface of the particles of the particulate hydrogel polymer (PC). This postcrosslinking can be effected thermally, photochemically or chemically.

Preferred postcrosslinkers are the compounds of crosslinker classes II and IV mentioned in connection with the crosslinkers ($\alpha$3).

Among these compounds, particularly preferred postcrosslinkers are diethylene glycol, triethylene glycol, polyethylene glycol, glycerol, polyglycerol, propylene glycol, diethanolamine, triethanolamine, polyoxypropylene, oxyethylene-oxypropylene block copolymers, sorbitan fatty acid esters, polyoxyethylenesorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, 1,3-dioxolan-2-one, poly-1,3-dioxolan-2-one.

Particular preference is given to using ethylene carbonate as the postcrosslinker.

Preferred embodiments of the water-absorbing polymers are those which are postcrosslinked by crosslinkers of the following crosslinker classes or by crosslinkers of the following combinations of crosslinker classes: II, IV and II IV.

The postcrosslinker is preferably used in an amount within a range from 0.01 to 30% by weight, more preferably in an amount within a range from 0.1 to 20% by weight and further preferably in an amount within a range from 0.3 to 5% by weight, based in each case on the weight of the superabsorbent polymers in the postcrosslinking.

It is likewise preferred that the postcrosslinking is effected by contacting a solvent comprising preferably water, water-miscible organic solvents, for instance methanol or ethanol or mixtures of at least two thereof, and the postcrosslinker with the outer region of the hydrogel polymer particles at a temperature within a range from 30 to 300° C., more preferably within a range from 100 to 200° C. The contacting is preferably effected by spraying the mixture consisting of postcrosslinker and solvent onto the hydrogel polymer particles and then mixing the hydrogel polymer particles contacted with the mixture. The postcrosslinker is present in the mixture preferably in an amount within a range from 0.01 to 20% by weight, more preferably in an amount within a range from 0.1 to 10% by weight, based on the total weight of the mixture. It is additionally preferred that contact with the hydrogel polymer particles is effected in an amount within a range from 0.01 to 50% by weight, more preferably in an amount within a range from 0.1 to 30% by weight, based in each case on the weight of the hydrogel polymer particles.

Useful condensation reactions preferably include the formation of ester, amide, imide or urethane bonds, preference being given to the formation of ester bonds.

The inventive hydrogel polymers and/or water-absorbing polymers can additionally be admixed with further additives and effect substances.

Preferred additives are additionally release agents, for instance inorganic or organic pulverulent release agents. These release agents are preferably used in amounts within a range from 0 to 2% by weight, more preferably within a range from 0.1 to 1.5% by weight, based on the weight of the hydrogel polymer and/or of the water-absorbing polymer. Preferred release agents are wood flour, pulp fibers, powdered bark, cellulose powder, mineral fillers such as perlite, synthetic fillers such as nylon powder, rayon powder, diatomaceous earth, bentonite, kaolin, zeolites, talc, loam, ash, carbon dust, magnesium silicates, fertilizers or mixtures of the substances. Finely divided fumed silica, as sold under the Aerosil trade name by Evonik Degussa, is preferred.

In a further preferred embodiment of the process according to the invention, the hydrogel polymer particles and/or the water-absorbing polymer particles are contacted with an effect substance, for example a polysugar, a polyphenolic compound, for example hydrolysable tannins or a compound containing silicon-oxygen, or a mixture of at least two effect substances based thereon. The effect substance can be added either in solid form (powder) or in dissolved form with a solvent, the effect substance being added not earlier than after process step iii). In the context of the present invention, an effect substance is understood to mean a substance which serves for odor inhibition.

According to the invention, this is understood to mean polysugars, by which the person skilled in the art understands those from the group of the familiar starches and derivatives thereof, celluloses and derivatives thereof, cyclodextrins. Cyclodextrins are preferably understood to mean α-cyclodextrin, β-cyclodextrin, γ-cyclodextrin or mixtures of these cyclodextrins.

Preferred compounds containing silicon-oxygen are zeolites. The zeolites used may be all synthetic or natural zeolites known to those skilled in the art. Preferred natural zeolites are zeolites from the natrolite group, the harmotome group, the mordenite group, the chabazite group, the faujasite group (sodalite group) or the analcite group. Examples of natural zeolites are analcime, leucite, pollucite, wairakite, bellbergite, bikitaite, boggsite, brewsterite, chabazite, willhendersonite, cowlesite, dachiardite, edingtonite, epistilbite, erionite, faujasite, ferrierite, amicite, garronite, gismondine, gobbinsite, gmelinite, gonnardite, goosecreekite, harmotome, phillipsite, wellsite, clinoptilolite, heulandite, laumontite, levyne, mazzite, merlinoite, montesommaite, mordenite, mesolite, natrolite, scolecite, offretite, paranatrolite, paulingite, perlialite, barrerite, stilbite, stellerite, thomsonite, tschernichite or yugawaralite. Preferred synthetic zeolites are zeolite A, zeolite X, zeolite Y, zeolite P, or the product ABSCENTS®.

The cations present in the zeolites used in the process according to the invention are preferably alkali metal cations such as $Li^+$, $Na^+$, $K^+$, $Rb^+$, $Cs^+$ or $Fr^+$ and/or alkaline earth metal cations such as $Mg^{2+}$, $Ca^{2+}$, $Sr^{2+}$ or $Ba^{2+}$.

The zeolites used may be zeolites of what is called the "intermediate" type, in which the $SiO_2/AlO_2$ ratio is less than 10; the $SiO_2/AlO_2$ ratio of these zeolites is more preferably within a range from 2 to 10. In addition to these "intermediate" zeolites, it is also possible to use zeolites of the "high" type, which include, for example, the known "molecular sieve" zeolites of the ZSM type, and beta-zeolite. These "high" zeolites are preferably characterized by an $SiO_2/AlO_2$ ratio of at least 35, more preferably by an $SiO_2/AlO_2$ ratio within a range from 200 to 500.

The zeolites are preferably used in the form of particles with a mean particle size within a range from 1 to 500 μm, more preferably within a range from 2 to 200 μm and further preferably within a range from 5 to 100 μm.

The effect substances are used in the processes according to the invention preferably in an amount within a range from 0.1 to 50% by weight, more preferably within a range from 1 to 40% by weight and further preferably in an amount within a range from 5 to 30% by weight, based in each case on the weight of the hydrogel polymer particles and/or water-absorbing polymer particles.

Preferred microbe-inhibiting substances are in principle all substances active against Gram-positive bacteria, for example 4-hydroxybenzoic acid and salts and esters thereof, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbonilide (TTC), antibacterial fragrances, thymol, thyme oil, eugenol, clove oil, menthol, mint oil, framesol, phenoxyethanol, glyceryl monocaprate, glyceryl monocaprylate, glyceryl monolaurate (GML), diglyceryl monocaprate (DMC), N-alkylsalicylamides, for example N-n-octylsalicylamide or N-n-decylsalicylamide.

Suitable enzyme inhibitors are, for example, esterase inhibitors. These are preferably trialkyl citrates such as trimethyl citrate, tripropyl citrate, triisopropyl citrate, tributyl citrate and especially triethyl citrate (Hydagen TM CAT, Cognis GmbH, Dusseldorf, Germany). The substances inhibit enzyme activity and as a result reduce odor formation. Further substances useful as esterase inhibitors are sterol sulphates or phosphates, for example lanosterol sulphate or phosphate, cholesterol sulphate or phosphate, campesterol sulphate or phosphate, stigmasterol sulphate or phosphate and sitosterol sulphate or phosphate, dicarboxylic acids and esters thereof, for example glutaric acid, monoethyl glutarate, diethyl glutarate, adipic acid, monoethyl adipate, diethyl adipate, malonic acid and diethyl malonate, hydroxycarboxylic acids and esters thereof, for example citric acid, malic acid, tartaric acid or diethyl tartrate, and zinc glycinate.

Suitable odor absorbers are substances which can adsorb and substantially retain odor-forming substances. They lower the partial pressure of the individual components and thus also reduce the rate of spread thereof. It is important that perfumes must remain unimpaired. Odor absorbers have no effect against bacteria. They contain, for example, as the main constituent, a complex zinc salt of ricinoleic acid or specific, substantially odor-neutral fragrances known to the person skilled in the art as "fixatives", for example extracts of labdanum or styrax or particular abietic acid derivatives. The function of odor maskers is fulfilled by odorants or perfume oils which, in addition to their function as odor maskers, impart their particular fragrance note to the deodorants. Examples of perfume oils include mixtures of natural and synthetic odorants. Natural odorants are extracts of flowers, stems and leaves, fruits, fruit skins, roots, woods, herbs and grasses, needles and twigs, and also resins and balsams. Additionally useful are animal raw materials, for example civet and castoreum. Typical synthetic odorant compounds are products of the ester, ether, aldehyde, ketone, alcohol and hydrocarbon type. Odorant compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether; the aldehydes include, for example, the linear alkanals having 8 to 18 carbon atoms, citral, citronellal, citronellyloxyacetaldehyde, cyclamen aldehyde, hydroxycitronellal, lilial and bourgeonal; the ketones include, for example, the ionones and methyl cedryl ketone; the alcohols include anethole, citronellol, eugenol, isoeugenol, geraniol, linalool, phenylethyl alcohol and terpineol; the hydrocarbons include principally the terpenes and balsams. Preference is given, however, to using mixtures of different odorants which together produce a pleasing fragrance note. Suitable perfume oils are also essential oils of relatively low volatility which are usually used as aroma components, for example sage oil, camomile oil, clove oil, melissa oil, mint oil, cinnamon leaf oil, lime blossom oil, juniperberry oil, vetiver oil, olibanum oil, galbanum oil, labdanum oil and lavender oil. Preference is given to using bergamot oil, dihydromyrcenol, lilial, lyral, citronellol, phenylethyl alcohol, alpha-hexylcinnamaldehyde, geraniol, benzylacetone, cyclamen aldehyde, linalool, Boisambrene Forte, ambroxan, indole, Hedione, Sandelice, lemon oil, mandarin oil, orange oil, allyl amyl glycolate, cyclovertal, lavender oil, clary sage oil, beta-damascone, geranium oil bourbon, cyclohexyl salicylate, Vertofix Coeur, Iso-E-Super, Fixolide NP, Evernyl, iraldein gamma, phenylacetic acid, geranyl acetate, benzyl acetate, rose oxide, Romilat, Irotyl and Floramat, alone or in mixtures.

Antiperspirants reduce the formation of perspiration by influencing the activity of the eccrine sweat glands, and thus counteract underarm wetness and body odor. Suitable astringent active antiperspirant ingredients are in particular salts of aluminum, zirconium or zinc. Such suitable antihydrotically active ingredients are, for example, aluminum chloride, aluminum chlorohydrate, aluminum dichlorohydrate, aluminum sesquichlorohydrate and the complexes thereof, for example with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and the complexes thereof, for example with amino acids such as glycine.

Suitable apparatus for mixing or spraying is any which allows homogeneous distribution of a solution, powder, suspension or dispersion on or with the hydrogel polymer particles (PC) or water-absorbing polymers. Examples are Lödige mixers (manufactured by Gebrüder Lödige Maschinenbau GmbH), Gericke multi-flux mixers (manufactured by Gericke GmbH), DRAIS mixers (manufactured by DRAIS GmbH Spezialmaschinenfabrik Mannheim), Hosokawa mixers (Hosokawa Mokron Co., Ltd.), Ruberg mixers (manufactured by Gebr. Ruberg GmbH & Co. KG Nieheim), Hüttlin coaters (manufactured by BWI Hüttlin GmbH Steinen), fluidized bed driers or spray granulators from AMMAG (manufactured by AMMAG Gunskirchen, Austria) or Heinen (manufactured by A. Heinen AG Anlagenbau Varel), Patterson-Kelly mixers, NARA paddle mixers, screw mixers, pan mixers, fluidized bed driers or Schugi mixers. For contacting in a fluidized bed, it is possible to employ all fluidized bed processes which are known to those skilled in the art and appear to be suitable. For example, it is possible to use a fluidized bed coater.

A further contribution to the achievement of the objects described at the outset is made by a composite including the inventive water-absorbing polymers or the hydrogel polymer, or the water-absorbing polymers or hydrogel polymers obtainable by the process according to the invention, and a substrate. It is preferable that the inventive water-absorbing polymers or hydrogel polymers and the substrate are bonded in a fixed manner to one another. Preferred substrates are films of polymers, for example of polyethylene, polypropylene or polyamide, metals, nonwovens, fluff, tissues, fabrics, natural or synthetic fibers, or foams. It is additionally preferred in accordance with the invention that the composite comprises at least one region which includes water-absorbing polymers or hydrogel polymers in an amount in the range from about 15 to 100% by weight, preferably about 30 to 100% by weight, more preferably from about 50 to 99.99% by weight, further preferably from about 60 to 99.99% by weight and even further preferably from about 70 to 99% by weight, based in each case on the total weight of the region of the composite in question, this region preferably having a size of at least 0.01 $cm^3$, preferably at least 0.1 $cm^3$ and most preferably at least 0.5 $cm^3$.

A further contribution to the achievement of at least one of the objects stated at the outset is made by a process for producing a composite, wherein the inventive water-absorbing polymers or the superabsorbents obtainable by the process according to the invention and a substrate and optionally an additive are contacted with one another. The substrates used are preferably those substrates which have already been mentioned above in connection with the inventive composite.

A contribution to the achievement of at least one of the objects stated at the outset is also made by a composite obtainable by the process described above, this composite preferably having the same properties as the above-described inventive composite.

A further contribution to the achievement of at least one of the objects stated at the outset is made by chemical products including the inventive water-absorbing polymers or hydrogel polymers or an inventive composite. Preferred chemical products are especially foams, moldings, fibers, foils, films, cables, sealing materials, liquid-absorbing hygiene articles, especially diapers and sanitary towels, carriers for plant growth or fungal growth regulators or plant protection active ingredients, additives for building materials, packaging materials or soil additives.

The use of the inventive water-absorbing polymers or of the inventive composite in chemical products, preferably in the aforementioned chemical products, especially in hygiene articles such as diapers or sanitary towels, and the use of the water-absorbing polymer particles as carriers for plant growth or fungal growth regulators or plant protection active ingredients make a contribution to the achievement of at least one of the objects stated at the outset. In the case of use as a carrier for plant growth or fungal growth regulators or plant protection active ingredients, it is preferred that the plant growth or fungal growth regulators or plant protection active ingredients can be released over a period controlled by the carrier.

Test Methods

Unless stated otherwise hereinafter, the measurements conducted herein are according to ERT methods. "ERT" stands for EDANA Recommended Test and "EDANA" for European Disposables and Nonwovens Association. All test methods are in principle, unless stated otherwise, conducted at an ambient temperature of 23±2° C. and a relative air humidity of 50±10%.

Particle Size Distribution (PSD)

The particle size distribution of the water-absorbing polymer particles is determined analogously to EDANA recommended test method No. WSP 220.3-10 "Particle Size Distribution".

Centrifuge Retention Capacity (CRC)

The centrifuge retention capacity was determined by EDANA (European Disposables and Nonwovens Association) recommended test method No. WSP 241.3-10 "Centrifuge retention capacity".

Determination of the Free Swell Rate (FSR)

The absorption rate was determined via the measurement of what is called the Free Swell Rate—(FSR) by the test method described in EP-A-0 443 627 on page 12.

Absorption Against a Pressure of 0.7 Psi (AAP)

The absorption under pressure was determined as the AAP (Absorption Against Pressure) to WSP 242.3-10 on the overall particle fraction. Accordingly, 0.90 g of the test substance (sieved off between 150 and 850 μm) were weighed into a test cylinder of internal diameter 60.0 mm with a sieve base (400 mesh) (concentration: 0.032 $g/cm^2$) and distributed homogeneously. A cylindrical weight (50 $g/cm^2$=0.7 psi) with an external diameter of 59.2 mm was placed onto the test substance. Filter plates were placed into a plastic dish, and were covered with a filter paper. The plastic dish was filled with 0.9% NaCl solution until the liquid level concludes with the upper edge of the filter plate. Subsequently, the prepared test units are placed onto the filter plates. After a swelling time of 60 minutes, the test units are withdrawn and the weight is removed. The amount of liquid absorbed is determined gravimetrically and converted to 1 gram of test substance.

Determination of Permeability (Saline Flow Conductivity—SFC)

The permeability is determined by the measurement of the "Saline Flow Conductivity-SFC" by the test method described in WO-A-95/26209. The starting weight of the superabsorbent material was 1.5 g rather than 0.9 g.

Determination of "Fixed Height Absorption" (FHA) (0.3 psi, 20 cm)

The determination is effected by measuring what is called the "fixed height absorption" (FHA) by the test method described in EP 149 34 53 A1 on page 9 [0078] to page 10 paragraph [0087].

Determination of Surface Tension (ST)

The determination is effected by the measurement according to the test method described in EP 1 493 453 A1, according to page 12 paragraphs [0105] to [0111]. A Kruss K11 tensiometer with a Wilhelmy plate was used.

Determination of the Extractable Polyether Fractions

The determination of the extractable fractions of the polyethers is based on the HPTLC method (H-III 14a dated 30 May 1995) Gemeinschaftsarbeiten der DGF 152. Mitteilung [German Society of Fat Science, Collaborative Studies, 152nd Communication]. The samples were ground, extracted with warm methanol in a Soxhlet extractor (1 hour), concentrated and then determined by thin-layer chromatography on silica gel 60 TLC plates of dimensions 20×20 cm. The samples are applied in a standardized manner. The eluent used was a mixture of chloroform/methanol/water (88/11/1 percent by volume). The derivatization was effected with Dragendorff's reagent. A Camag CD60 TLC scanner with a measurement wavelength of 520 nm was used. The evaluation was effected via the peak areas, which were expressed as a ratio relative to the peak areas of the standards.

Determination of the BET Surface Area

The BET surface area of the superabsorbents was determined by means of a tristar 3020 Kr instrument from Micromeritics (with krypton gas rather than nitrogen), analogously to ISO 9277. The starting weight was 4.6 g and was evacuated at room temperature and a vacuum of 0.02 mbar overnight and reweighed. Evacuation was effected using the analysis port, the evacuation being effected over a period of 6 minutes when 10 mm of Hg has been attained. The dead volume was likewise determined. The analysis temperature was 77.1 K. p0 was defined as 2.32 mm of Hg (using krypton gas). The equilibration time was measured at least 10 times (5 sec, at a rate of change of less than 0.01%).

EXAMPLES

The examples which follow serve for further illustration of the invention, but without restricting it thereto.

to 710 µm. The PSD is established for the hydrogel polymers.

EPI 701786 B1, in paragraphs [0115 to 0117], defines the mass average of the particle diameter D50. According to the invention, preference is given to a range between 300 and 600 µm. Particular preference is given to a range from 350 to 550 µm, and very particular preference to a range between 400 and 500 µm.

Preference is given to a blowing agent in which more than 35% by weight of the particles have a particle size of 100-300 µm.

The term "SX" as used in the description is understood to mean the thermal surface postcrosslinking of the precursor (PC). The precursor corresponds to the hydrogel polymer obtained after the first drying, with the aforementioned particle distribution.

In principle, the percentages for the surfactant are based on the acrylic acid (unless stated otherwise, 320 g) and those for the carbonate on the mixture (1000 g).

Example 1

Surfactant No. 1, "allyl-10EO-b-10PO-acetyl", from Table 1 was used as the additive. The amounts of surfactant used and carbonate varied.

Use without polymerizable surfactant and sodium carbonate:

Example 1A

Reference 0.775 g of polyethylene glycol-300 diacrylate (PEG300DA) (0.2% based on acrylic acid/ester content,

TABLE 1

| Surfactant - Example No. | Name (supplier) | Description (incl. sequence of the blocks) | $n$(EO) | $m$(PO) | R |
|---|---|---|---|---|---|
| 1 | PE7089 (Evonik Industries) | allyl-10EO-b-10PO-acetyl | 10 | 10 | —C(=O)CH$_3$ |
| 2 | PE7087 (Evonik Industries) | allyl-10PO-b-10EO-acetyl | 10 | 10 | —C(=O)CH$_3$ |
| 3 | PE7086 (Evonik Industries) | allyl-10EO-b-10PO-methyl | 10 | 10 | —CH$_3$ |
| 4 | Pluriol ® A111 R (BASF) | allyl-iEO-b-jPO-methyl | — | — | —CH$_3$ |
| 5 | PE7514 (Evonik Industries) | allyl-6EO-b-6PO-acetyl | 6 | 6 | —C(=O)CH$_3$ |
| 6 | PE7316/02 (Evonik Industries) | allyl-6EO-b-6PO-hydroxyl | 6 | 6 | —H |
| 7 | Pluriol ® A23 R (BASF) | allyl-qEO-b-rPO-hydroxyl | — | — | —H |
| 8 | PE7065 (Evonik Industries) | allyl-10PO-b-20EO-hydroxyl | 20 | 10 | —H |
| 9 | PE7081 (Evonik Industries) | allyl-10PO-b-20EO-methyl | 20 | 10 | —CH$_3$ |
| 10 | sodium laurylethersulphate (Hansa-Group) | sodium laurylethersulphate | — | — | — |

The inventive examples which follow show the synergistic effect on the FSR value by the simultaneous use of polymerizable surfactants and carbonate. In this context, a defined particle size distribution (PSD) was used (150 µm to 710 µm). The standard mixture used is a composition of 4 particle fractions prior to surface crosslinking, which have the following distribution: 15% by weight of a particle size of from 150 µm to 300 µm; 50% by weight 300 µm to 500 µm; 30% by weight 500 µm to 600 µm and 5% by weight 600 µm corresponding to 83%) and 1.639 g of polyethylene glycol-440 monoallyl ether acrylate (PEGMAE-A) (0.4% based on acrylic acid/ester content, corresponding to 78%) as crosslinker were dissolved in 975.201 g of an aqueous solution of sodium acrylate with a neutralization level of 70 mol % (based on acrylic acid) and a total monomer concentration of 39.82%. The monomer solution was purged with nitrogen in a plastic polymerization vessel for 30 minutes in order to remove the dissolved oxygen. At a temperature of 4° C., the polymerization was initiated by the successive addition of 0.3 g of sodium peroxodisulphate in 10 g of dist. water, 0.07 g of 35% hydrogen peroxide solution in 10 g of dist. water and 0.015 g of ascorbic acid in 2 g of dist. water. Once the end temperature (approx. 100° C.) had been attained, the gel was comminuted with a meat grinder and dried at 150° C. in a forced-air drying cabinet for 2 h. The dried precursor was coarsely crushed, ground and adjusted to the above-described particle distribution.

Example 1B

2nd Reference 0.697 g of polyethylene glycol-300 diacrylate (0.18% based on acrylic acid/ester content=83%) and 1.475 g of polyethylene glycol-440 monoallyl ether acrylate (0.36% based on acrylic acid/ester content, corresponding to 78%) as crosslinker were dissolved in 975.443 g of an aqueous solution of sodium acrylate with a neutralization level of 70 mol % (based on acrylic acid) and a total monomer concentration of 39.81%. The monomer solution was purged with nitrogen in a plastic polymerization vessel for 30 minutes in order to remove the dissolved oxygen. At a temperature of 4° C., the polymerization was initiated by the successive addition of 0.3 g of sodium peroxodisulphate in 10 g of dist. water, 0.07 g of 35% hydrogen peroxide solution in 10 g of dist. water and 0.015 g of ascorbic acid in 2 g of dist. water. Once the end temperature (approx. 100° C.) had been attained, the gel was comminuted with a meat grinder and dried at 150° C. in a forced-air drying cabinet for 2 h. The dried precursor was coarsely crushed, ground and adjusted to the above-described particle distribution.

Use without polymerizable surfactant and with 0.2% light sodium carbonate:

Example 1C 0.697 g of polyethylene glycol-300 diacrylate (0.18% based on acrylic acid/ester content=83%) and 1.475 g of polyethylene glycol-440 monoallyl ether acrylate (0.36% based on acrylic acid/ester content, corresponding to 78%) as crosslinker were dissolved in 973.443 g of an aqueous solution of sodium acrylate with a neutralization level of 70 mol % (based on acrylic acid) and a total monomer concentration of 39.89%. The monomer solution was purged with nitrogen in a plastic polymerization vessel for 30 minutes in order to remove the dissolved oxygen. At a temperature of 4° C., 2 g of finely calcined sodium carbonate (from Solvay) were added and the polymerization was initiated by the successive addition of 0.3 g of sodium peroxodisulphate in 10 g of dist. water, 0.07 g of 35% hydrogen peroxide solution in 10 g of dist. water and 0.015 g of ascorbic acid in 2 g of dist. water. Once the end temperature (approx. 100° C.) had been attained, the gel was comminuted with a meat grinder and dried at 150° C. in a forced-air drying cabinet for 2 h. The dried precursor was coarsely crushed, ground and adjusted to the above-described particle distribution.

Use of 0.3% polymerizable surfactant:

Example 1D 0.775 g of polyethylene glycol-300 diacrylate (0.2% based on acrylic acid/ester content=83%) and 1.639 g of polyethylene glycol-440 monoallyl ether acrylate (0.4% based on acrylic acid/ester content, corresponding to 78%) as crosslinker were dissolved in 965.601 g of an aqueous solution of sodium acrylate with a neutralization level of 70 mol % (based on acrylic acid) and a total monomer concentration of 40.22%. Subsequently, 9.6 g of a 10% aqueous solution of comonomer No. 1 "allyl-10EO-b-10PO-acetyl" were added to this solution and the monomer solution was purged with nitrogen in a plastic polymerization vessel for 30 minutes in order to remove the dissolved oxygen. At a temperature of 4° C., the polymerization was initiated by the successive addition of 0.3 g of sodium peroxodisulphate in 10 g of dist. water, 0.07 g of 35% hydrogen peroxide solution in 10 g of dist. water and 0.015 g of ascorbic acid in 2 g of dist. water. Once the end temperature (approx. 100° C.) had been attained, the gel was comminuted with a meat grinder and dried at 150° C. in a forced-air drying cabinet for 2 h. The dried precursor was coarsely crushed, ground and adjusted to the above-described particle distribution.

Use of 0.3% polymerizable surfactant and 0.2% light sodium carbonate:

Example 1E 0.697 g of polyethylene glycol-300 diacrylate (0.18% based on acrylic acid/ester content=83%) and 1.475 g of polyethylene glycol-440 monoallyl ether acrylate (0.36% based on acrylic acid/ester content, corresponding to 78%) as crosslinker were dissolved in 963.843 g of an aqueous solution of sodium acrylate with a neutralization level of 70 mol % (based on acrylic acid) and a total monomer concentration of 40.29%. Subsequently, 9.6 g of a 10% aqueous solution of comonomer No. 1 "allyl-100EO-b-10PO-acetyl" were added to this solution and the monomer solution was purged with nitrogen in a plastic polymerization vessel for 30 minutes in order to remove the dissolved oxygen. At a temperature of 4° C., 2 g of finely calcined sodium carbonate (from Solvay) were added and the polymerization was initiated by the successive addition of 0.3 g of sodium peroxodisulphate in 10 g of dist. water, 0.07 g of 35% hydrogen peroxide solution in 10 g of dist. water and 0.015 g of ascorbic acid in 2 g of dist. water. Once the end temperature (approx. 100° C.) had been attained, the gel was comminuted with a meat grinder and dried at 150° C. in a forced-air drying cabinet for 2 h. The dried precursor was coarsely crushed, ground and adjusted to the above-described particle distribution.

The surface postcrosslinking of the precursors thus obtained ("PC") was effected by coating with a solution consisting of ethylene carbonate/water/aluminum lactate/aluminum sulphate in a ratio of 1/3/0.4/0.3% based on 100 g of precursor and subsequent heating at 170° C. over a period of 90 min in a drying cabinet.

The results for Examples 1A-1E are summarized in Table 2:

TABLE 2

| Example No. | Surfactant monomer added | Light sodium carbonate added | CRC (PC) [g/g] | CRC (SX) [g/g] | FSR (SX) [g/g/s] | ST [mN/m] | AAP 0.7 psi [g/g] | SFC 1.5 g [units] | FHA [g/g] |
|---|---|---|---|---|---|---|---|---|---|
| 1A | 0% | 0% | 30.8 | 25.9 | 0.29 | 70.1 | 24.6 | 123 | 22.1 |
| 1B | 0% | 0% | 31.3 | 25.9 | 0.28 | 70.8 | 25.0 | 107 | 22.4 |

TABLE 2-continued

| Example No. | Surfactant monomer added | Light sodium carbonate added | CRC (PC) [g/g] | CRC (SX) [g/g] | FSR (SX) [g/g/s] | ST [mN/m] | AAP 0.7 psi [g/g] | SFC 1.5 g [units] | FHA [g/g] |
|---|---|---|---|---|---|---|---|---|---|
| 1C | 0% | 0.2% | 31.5 | 28.3 | 0.46 | 68.6 | 25.7 | 83 | 23.3 |
| 1D | 0.3% | 0% | 31.3 | 26.0 | 0.35 | 54.4 | 24.4 | 75 | 20.9 |
| 1E | 0.3% | 0.2% | 31.4 | 26.0 | 0.56 | 54.7 | 24.9 | 91 | 24.1 |

Example 2

The experimental setup corresponded to Example 1, except that the surfactant used was allyl-10PO-b-10EO-acetyl (PE7087, Evonik Industries). The amounts of the surfactant and carbonate used varied. The surface postcrosslinking of the precursors thus obtained was effected by coating with a solution consisting of ethylene carbonate/water/aluminum lactate/aluminum sulphate in a ratio of 1/3/0.4/0.3% based on 100 g of precursor and subsequent heating at 170° C. over a period of 90 min in a drying cabinet.

The results for Examples 2D and 2E were summarized in Table 3:

TABLE 3

| Example No. | Surfactant monomer added | Light sodium carbonate added | CRC (PC) [g/g] | CRC (SX) [g/g] | FSR (SX) [g/g/s] | ST [mN/m] | AAP 0.7 psi [g/g] | SFC 1.5 g [units] | FHA [g/g] |
|---|---|---|---|---|---|---|---|---|---|
| 1A | 0% | 0% | 30.8* | 25.9 | 0.29 | 70.1 | 24.6 | 123 | 22.1 |
| 1B | 0% | 0% | 31.3** | 25.9 | 0.28 | 70.8 | 25.0 | 107 | 22.4 |
| 1C | 0% | 0.2% | 31.5** | 28.3 | 0.46 | 68.6 | 25.7 | 83 | 23.3 |
| 2D | 0.3% | 0% | 31.6* | 26.1 | 0.36 | 53.5 | 24.6 | 102 | 17.9 |
| 2E | 0.3% | 0.2% | 31.6** | 26.2 | 0.59 | 52.3 | 24.6 | 93 | 23.0 |

*PEG300DA/PEGMAE-A crosslinking: 0.2%/0.4% based on acrylic acid
**PEG300DA/PEGMAE-A crosslinking: 0.18%/0.36% based on acrylic acid Example 3

The experimental setup corresponded to Example 1, except that the surfactant used was allyl-10EO-b-10PO-acetyl (PE7086, Evonik Industries). The amounts of the surfactant and carbonate used varied. The surface postcrosslinking of the precursors thus obtained was effected by coating with a solution consisting of ethylene carbonate/water/aluminum lactate/aluminum sulphate in a ratio of 1/3/0.4/0.3% based on 100 g of precursor and subsequent heating at 170° C. over a period of 90 min in a drying cabinet.

The results for Examples 3D and 3E are summarized in Table 4:

TABLE 4

| Example No. | Surfactant monomer added | Light sodium carbonate added | CRC (PC) [g/g] | CRC (SX) [g/g] | FSR (SX) [g/g/s] | ST [mN/m] | AAP 0.7 psi [g/g] | SFC 1.5 g [units] | FHA [g/g] |
|---|---|---|---|---|---|---|---|---|---|
| 1A | 0% | 0% | 30.8* | 25.9 | 0.29 | 70.1 | 24.6 | 123 | 22.1 |
| 1B | 0% | 0% | 31.3** | 25.9 | 0.28 | 70.8 | 25.0 | 107 | 22.4 |
| 1C | 0% | 0.2% | 31.5** | 28.3 | 0.46 | 68.6 | 25.7 | 83 | 23.3 |
| 3D | 0.3% | 0% | 31.4* | 26.7 | 0.30 | 55.2 | 24.5 | 123 | 19.5 |
| 3E | 0.3% | 0.2% | 32.0** | 27.3 | 0.56 | 55.7 | 25.3 | 76 | 25.1 |

*PEG300DA/PEGMAE-A crosslinking: 0.2%/0.4% based on acrylic acid
**PEG300DA/PEGMAE-A crosslinking: 0.18%/0.36% based on acrylic acid Example 4

The experimental setup corresponded to Example 1, except that the additive used was Pluriol® A111 R (BASF). The amounts of surfactant used and carbonate varied.

Use of 0.3% polymerizable surfactant and 0.2% light sodium carbonate:

Example 4D 0.775 g of polyethylene glycol-300 diacrylate (0.2% based on acrylic acid/ester content, corresponding to 83%) and 1.639 g of polyethylene glycol-440 monoallyl ether acrylate (0.4% based on acrylic acid/ester content, corresponding to 78%) as crosslinker were dissolved in 963.601 g of an aqueous solution of sodium acrylate with a neutralization level of 70 mol % (based on acrylic acid) and a total monomer concentration of 40.30%. Subsequently, 9.6 g of a 10% aqueous solution of comonomer No. 4 Pluriol® A111 R (BASF) were added to this solution and the monomer solution was purged with nitrogen in a plastic polymerization vessel for 30 minutes in order to remove the dissolved oxygen. At a temperature of 4° C., 2 g of finely calcined sodium carbonate (from Solvay) were added and the polymerization was initiated by the successive addition of 0.3 g of sodium peroxodisulphate in 10 g of dist. water, 0.07 g of 35% hydrogen peroxide solution in 10 g of dist. water and 0.015 g of ascorbic acid in 2 g of dist. water. Once the end temperature (approx. 100° C.) had been attained, the gel was comminuted with a meat grinder and dried at 150° C. in a forced-air drying cabinet for 2 h. The dried precursor was coarsely crushed, ground and sieved to size.

The surface postcrosslinking of the precursors thus obtained (PC) was effected by coating with a solution consisting of ethylene carbonate/water/aluminum lactate/aluminum sulphate in a ratio of 1/3/0.4/0.3% based on 100 g of precursor and subsequent heating at 170° C. over a period of 90 min in a drying cabinet.

The results for Examples 4A-4E are summarized in Table 5:

tion vessel for 30 minutes in order to remove the dissolved oxygen. At a temperature of 4° C., the polymerization was initiated by the successive addition of 0.3 g of sodium peroxodisulphate in 10 g of dist. water, 0.07 g of 35% hydrogen peroxide solution in 10 g of dist. water and 0.015 g of ascorbic acid in 2 g of dist. water. Once the end temperature (approx. 100° C.) had been attained, the gel was comminuted with a meat grinder and dried at 150° C. in a forced-air drying cabinet for 2 h. The dried precursor was coarsely crushed, ground and sieved to size.

The surface postcrosslinking of the precursors thus obtained was effected by coating with a solution consisting of ethylene carbonate/water/aluminum lactate/aluminum

TABLE 5

| Example No. | Surfactant monomer added | Light sodium carbonate added | CRC (PC) [g/g] | CRC (SX) [g/g] | FSR (SX) [g/g/s] | ST [mN/m] | AAP 0.7 psi [g/g] | SFC 1.5 g [units] | FHA [g/g] |
|---|---|---|---|---|---|---|---|---|---|
| 1A | 0% | 0% | 30.8* | 25.9 | 0.29 | 70.1 | 24.6 | 123 | 22.1 |
| 1C | 0% | 0.2% | 31.5 | 28.3 | 0.46 | 68.6 | 25.7 | 83 | 23.3 |
| 4C | 0.3% | 0% | 29.2* | 25.8 | 0.39 | 52.5 | 25.6 | 126 | 22.6 |
| 4D | 0.3% | 0.2% | 29.1* | 26.4 | 0.54 | 52.1 | 25.6 | 67 | 22.4 |
| 4E | 0.3% | 0.2% | 32.1** | 27.6 | 0.51 | 51.5 | 26.0 | 43 | 21.2 |

*PEG300DA/PEGMAE-A crosslinking: 0.2%/0.4% based on acrylic acid
**PEG300DA/PEGMAE-A crosslinking: 0.18%/0.36% based on acrylic acid Example 5

The experimental setup corresponded to Example 1, except that the surfactant used was allyl-6EO-b-6PO-acetyl (PE7514, Evonik Industries). The amounts of surfactant used and carbonate varied.

Use of 0.3% polymerizable surfactant and 0% light sodium carbonate:

sulphate in a ratio of 1/3/0.4/0.3% based on 100 g of precursor and subsequent heating at 170° C. over a period of 90 min in a drying cabinet.

The results for Examples 5C-5E are summarized in Table 6:

TABLE 6

| Example No. | Surfactant monomer added | Light sodium carbonate added | CRC (PC) [g/g] | CRC (SX) [g/g] | FSR (SX) [g/g/s] | ST [mN/m] | AAP 0.7 psi [g/g] | SFC 1.5 g [units] | FHA [g/g] |
|---|---|---|---|---|---|---|---|---|---|
| 1A | 0% | 0% | 30.8* | 25.9 | 0.29 | 70.1 | 24.6 | 123 | 22.1 |
| 1C | 0% | 0.2% | 31.5 | 28.3 | 0.46 | 68.6 | 25.7 | 83 | 23.3 |
| 5C | 0.2% | 0.2% | 31.4** | 27.3 | 0.52 | 58.8 | 26.0 | 93 | 20.6 |
| 5D | 0.3% | 0% | 29.8* | 25.6 | 0.40 | 57.5 | 25.1 | 114 | 23.1 |
| 5E | 0.3% | 0.2% | 30.4** | 26.3 | 0.59 | 57.8 | 26.0 | 74 | 22.3 |

*PEG300DA/PEGMAE-A crosslinking: 0.2%/0.4% based on acrylic acid
**PEG300DA/PEGMAE-A crosslinking: 0.18%/0.36% based on acrylic acid Example 5D 0.697 g of polyethylene glycol-300 diacrylate (0.18% based on acrylic acid/ester content, corresponding to 83%) and 1.475 g of polyethylene glycol-440 monoallyl ether acrylate (0.36% based on acrylic acid/ester content, corresponding to 78%) as crosslinker were dissolved in 965.843 g of an aqueous solution of sodium acrylate with a neutralization level of 70 mol % (based on acrylic acid) and a total monomer concentration of 40.21%. Subsequently, 9.6 g of a 10% aqueous solution of comonomer No. 5 allyl-6EO-b-6PO-acetyl were added to this solution and the monomer solution was purged with nitrogen in a plastic polymeriza- Example 6

The experimental setup corresponded to Example 1, except that the surfactant used was allyl-6EO-b-6PO-hydroxyl (PE7316/02, Evonik Industries). The amounts of surfactant used and carbonate varied. The surface postcrosslinking of the precursors thus obtained was effected by coating with a solution consisting of ethylene carbonate/water/aluminum lactate/aluminum sulphate in a ratio of 1/3/0.4/0.3% based on 100 g of precursor and subsequent heating at 170° C. over a period of 90 min in a drying cabinet.

The results for Examples 6C-6E are summarized in Table 7:

TABLE 7

| Example No. | Surfactant monomer added | Light sodium carbonate added | CRC (PC) [g/g] | CRC (SX) [g/g] | FSR (SX) [g/g/s] | ST [mN/m] | AAP 0.7 psi [g/g] | SFC 1.5 g [units] | FHA [g/g] |
|---|---|---|---|---|---|---|---|---|---|
| 1A | 0% | 0% | 30.8* | 25.9 | 0.29 | 70.1 | 24.6 | 123 | 22.1 |
| 1C | 0% | 0.2% | 31.5 | 28.3 | 0.46 | 68.6 | 25.7 | 83 | 23.3 |
| 6C | 0.2% | 0.2% | 30.7* | 26.8 | 0.53 | 60.0 | 25.8 | 74 | 24.6 |
| 6D | 0.3% | 0% | 31.1* | 26.5 | 0.37 | 60.8 | 24.8 | 92 | 23.1 |
| 6E | 0.3% | 0.2% | 31.7** | 26.6 | 0.60 | 59.8 | 25.2 | 81 | 25.2 |

*PEG300DA/PEGMAE-A crosslinking: 0.2%/0.4% based on acrylic acid
**PEG300DA/PEGMAE-A crosslinking: 0.18%/0.36% based on acrylic acid Example 7

The experimental setup corresponded to Example 1, except that the additive used was Pluriol® A111 R (BASF). The amounts of surfactant used and carbonate varied. The surface postcrosslinking of the precursors thus obtained was effected by coating with a solution consisting of ethylene carbonate/water/aluminum lactate/aluminum sulphate in a ratio of 1/3/0.4/0.3% based on 100 g of precursor and subsequent heating at 170° C. over a period of 90 min in a drying cabinet.

The results for Examples 7C-7F are summarized in Table 8:

TABLE 8

| Example No. | Surfactant monomer added | Light sodium carbonate added | CRC (PC) [g/g] | CRC (SX) [g/g] | FSR (SX) [g/g/s] | ST [mN/m] | AAP 0.7 psi [g/g] | SFC 1.5 g [units] | FHA [g/g] |
|---|---|---|---|---|---|---|---|---|---|
| 1A | 0% | 0% | 30.8* | 25.9 | 0.29 | 70.1 | 24.6 | 123 | 22.1 |
| 1C | 0% | 0.2% | 31.5 | 28.3 | 0.46 | 68.6 | 25.7 | 83 | 23.3 |
| 7C | 0.1% | 0.2% | 29.9* | 25.8 | 0.56 | 62.5 | 25.4 | 90 | 24.4 |
| 7D | 0.3% | 0% | 30.3* | 26.0 | 0.35 | 65.0 | 25.5 | 115 | 23.9 |
| 7E | 0.3% | 0.2% | 30.7** | 27.9 | 0.56 | 64.0 | 26.4 | 64 | 25.2 |
| 7F | 0.3% | 0.2% | 30.0* | 26.4 | 0.62 | 63.4 | 25.4 | 77 | 24.6 |

*PEG300DA/PEGMAE-A crosslinking: 0.2%/0.4% based on acrylic acid
**PEG300DA/PEGMAE-A crosslinking: 0.18%/0.36% based on acrylic acid Example 8

The experimental setup corresponded to Example 1, except that the surfactant used was allyl-10PO-b-20EO-hydroxyl (PE7065, Evonik Industries). The amounts of surfactant used and carbonate varied. The surface postcrosslinking of the precursors thus obtained was effected by coating with a solution consisting of ethylene carbonate/water/aluminum lactate/aluminum sulphate in a ratio of 1/3/0.4/0.3% based on 100 g of superabsorbent and subsequent heating at 170° C. over a period of 90 min in a drying cabinet.

The results for Examples 8D-8E are summarized in Table 9:

TABLE 9

| Example No. | Surfactant monomer added | Light sodium carbonate added | CRC (PC) [g/g] | CRC (SX) [g/g] | FSR (SX) [g/g/s] | ST [mN/m] | AAP 0.7 psi [g/g] | SFC 1.5 g [units] | FHA [g/g] |
|---|---|---|---|---|---|---|---|---|---|
| 1A | 0% | 0% | 30.8* | 25.9 | 0.29 | 70.1 | 24.6 | 123 | 22.1 |
| 1B | 0% | 0% | 31.3** | 25.9 | 0.28 | 70.8 | 25.0 | 107 | 22.4 |
| 1C | 0% | 0.2% | 31.5** | 28.3 | 0.46 | 68.6 | 25.7 | 83 | 23.3 |
| 8D | 0.3% | 0% | 33.1* | 29.1 | 0.40 | 55.8 | 25.0 | 80 | 24.4 |
| 8E | 0.3% | 0.2% | 33.0** | 27.9 | 0.65 | 55.2 | 25.7 | 81 | 23.8 |

*PEG300DA/PEGMAE-A crosslinking: 0.2%/0.4% based on acrylic acid
**PEG300DA/PEGMAE-A crosslinking: 0.18%/0.36% based on acrylic acid

Example 9

The experimental setup corresponded to Example 1, except that the surfactant used was allyl-10PO-b-20EO-acetyl (PE7081, Evonik Industries). The amounts of surfactant used and carbonate varied. The surface postcrosslinking of the precursors thus obtained was effected by coating with a solution consisting of ethylene carbonate/water/aluminum lactate/aluminum sulphate in a ratio of 1/3/0.4/0.3% based on 100 g of precursor and subsequent heating at 170° C. over a period of 90 min in a drying cabinet.

The results for Examples 9D-9E are summarized in Table 10:

TABLE 10

| Example No. | Surfactant monomer added | Light sodium carbonate added | CRC (PC) [g/g] | CRC (SX) [g/g] | FSR (SX) [g/g/s] | ST [mN/m] | AAP 0.7 psi [g/g] | SFC 1.5 g [units] | FHA [g/g] |
|---|---|---|---|---|---|---|---|---|---|
| 1A | 0% | 0% | 30.8* | 25.9 | 0.29 | 70.1 | 24.6 | 123 | 22.1 |
| 1B | 0% | 0% | 31.3** | 25.9 | 0.28 | 70.8 | 25.0 | 107 | 22.4 |
| 1C | 0% | 0.2% | 31.5** | 28.3 | 0.46 | 68.6 | 25.7 | 83 | 23.3 |
| 9D | 0.3% | 0% | 31.3* | 28.0 | 0.40 | 55.8 | 24.9 | 102 | 24.3 |
| 9E | 0.3% | 0.2% | 32.2** | 28.4 | 0.55 | 56.1 | 25.3 | 90 | 24.7 |

*PEG300DA/PEGMAE-A crosslinking: 0.2%/0.4% based on acrylic acid
**PEG300DA/PEGMAE-A crosslinking: 0.18%/0.36% based on acrylic acid

Example 10

Comparative Example

The experimental setup corresponded to Example 1, except that the surfactant used was sodium laurylethersulphate (Hansa-Group AG, Duisburg). NaLES is a surfactant which is not incorporable by polymerization. The amounts of surfactant used and carbonate varied.

The surface postcrosslinking of the precursors thus obtained was effected by coating with a solution consisting of ethylene carbonate/water/aluminum lactate/aluminum sulphate in a ratio of 1/3/0.4/0.3% based on 100 g of precursor and subsequent heating at 170° C. over a period of 90 min in a drying cabinet.

The results for Examples 100D-100E are summarized in Table 11:

TABLE 11

| Example No. | Surfactant monomer added | Light sodium carbonate added | CRC (PC) [g/g] | CRC (SX) [g/g] | FSR (SX) [g/g/s] | ST [mN/m] | AAP 0.7 psi [g/g] | SFC 1.5 g [units] | FHA [g/g] |
|---|---|---|---|---|---|---|---|---|---|
| 1A | 0% | 0% | 30.8* | 25.9 | 0.29 | 70.1 | 24.6 | 123 | 22.1 |
| 1B | 0% | 0% | 31.3** | 25.9 | 0.28 | 70.8 | 25.0 | 107 | 22.4 |
| 1C | 0% | 0.2% | 31.5** | 28.3 | 0.46 | 68.6 | 25.7 | 83 | 23.3 |
| 10D | 0.3% | 0% | 31.6* | 28.3 | 0.42 | 38.0 | 24.9 | 68 | 16.2 |
| 10E | 0.3% | 0.2% | 32.8** | 28.2 | 0.57 | 37.5 | 25.2 | 62 | 16.3 |

*PEG300DA/PEGMAE-A crosslinking: 0.2%/0.4% based on acrylic acid
**PEG300DA/PEGMAE-A crosslinking: 0.18%/0.36% based on acrylic acid In the case of the surfactant not incorporable by polymerization, a considerable deterioration in the FHA value was found.

The ST values of the water-absorbing polymers according to the above-described inventive examples are more than 50 mN/m, preferably more than 55 mN/m, more preferably more than 60 mN/m and most preferably more than 62 mN/m. The ST value must not exceed a value of 68 nM/m. Advantageously, this minimizes the rewet value (e.g. backsheet rewet) in the diapers and maintains the capillarity of the superabsorbent in the absorbent core of the diapers, which thus correspond to high FHA values. The use of short EO and PO blocks in the surfactant comonomers avoids significant lowering of the ST values.

Advantageously, the simultaneous use of the surfactant comonomers and carbonate leads to a synergistic increase in the values of the FSR and of the FHA. According to the invention, the aforementioned effect is found particularly in the case of water-absorbing polymers having an ST value greater than 60. The inventive water-absorbing polymers additionally exhibit good parameter properties with regard to the CRC, SFC and AAP values.

According to the table below, it has been shown that, in accordance with the invention, the copolymerizable surfactants ("surfactant monomers", SM) have been incorporated into the network of the hydrogel polymer. The extractables are reported in the last column of the table. The amount of extractable polyether fractions based on the total amount of copolymerizable surfactants (SM) used for the polymerization in % has been examined here. According to the invention, less than 10% extractable surfactants/surfactant monomers was always found. This showed that the surfactant has been incorporated into the polymer matrix of the superabsorbent.

| Example No. | Extractable polyether fraction (ppm) | % based on amount of polyether used |
|---|---|---|
| 1A | <10 ppm | — |
| 1D | 60 | 2.4% |

-continued

| Example No. | Extractable polyether fraction (ppm) | % based on amount of polyether used |
|---|---|---|
| 5D | 150 | 6% |
| 7D | 85 | 3.4% |
| 8D | 90 | 3.6% |
| 9D | 70 | 2.8% |

From the measurements of the BET surface area, it was surprisingly possible to show that the inventive hydrogel polymers have up to an 18% increase in BET surface area from the reference hydrogel polymers without surfactants and sodium carbonate.

Results of the BET measurements:

| Example No. | Surfactant monomer added | Light sodium carbonate added | BET [m²/g] | % increase compared to reference |
|---|---|---|---|---|
| 1B | 0% | 0% | 0.0296 | reference |
| 4B | 0% | 0.2% | 0.0320 | +8% |
| 7E | 0.3% | 0.2% | 0.0348 | +18% |

The invention claimed is:

1. A process for producing a water-absorbing polymer composition, comprising the process steps of
   (i) mixing
      (α1) 0.1 to 99.999% by weight of polymerizable, ethylenically unsaturated monomers containing acid groups, or salts thereof, or polymerizable, ethylenically unsaturated monomers including a protonated or quaternized nitrogen, or mixtures thereof, particular preference being given to mixtures including at least ethylenically unsaturated monomers containing acid groups,
      (α2) 0 to 70% by weight of polymerizable, ethylenically unsaturated monomers copolymerizable with (α1),
      (α3) 0.001 to 10% by weight of one or more crosslinkers,
      (α4) 0 to 30% by weight of water-soluble polymers, and
      (α5) 0 to 20% by weight of one or more assistants, where the sum of the weights of (α1) to (α5) is 100% by weight,
      to form an aqueous monomer solution,
   (ii) adding an initiator to promote free-radical polymerization with crosslinking to form a water-insoluble, aqueous untreated hydrogel polymer,
   (iii) drying the hydrogel polymer,
   (iv) grinding and sieving the hydrogel polymer to size,
   (v) surface postcrosslinking the ground and sieved hydrogel polymer and
   (vi) drying and finishing the water-absorbing polymer,
   wherein the aqueous monomer solution, prior to the addition of the initiator and the commencement of free-radical polymerization, is admixed with 0.01 to 5% by weight of at least one surfactant, based on the monomer containing acid group, from the group of the nonionic, ionic or amphoteric surfactants which are copolymerizable with the monomers specified in (α1) and optionally 0.01 to 5% by weight of a blowing agent having a particle size of 10 µm to 900 µm, based on the water-absorbing polymer composition; the Free Swell Rate (FSR) is in the range of from 0.3 to 0.65 g/g/s and the surface tension (ST) is above 50 mN/m.

2. The process according to claim 1, characterized in that the aqueous monomer solution at least one surfactant from the group of the nonionic, ionic or amphoteric surfactants and 0.01 to 5% by weight of blowing agent with a particle size of 10 µm to 900 µm added are, based on the water-absorbing polymer.

3. The process according to claim 1, characterized in that the surfactant is preferably selected from the group of the nonionic surfactants.

4. The process according to claim 1, characterized in that the surfactant is selected from the group of $R^1$-(EO)$_n$-block-(PO)$_m$—$R^2$ where $R^1$ or $R^2$ is a methyl, ethyl, n-propyl, isopropyl, n-butyl, isobutyl, n-pentyl, 2-methylbutyl, 2,2-dimethylpropyl, —OH, acetyl or allyl radical and n=2 to 20 and m=2 to 20.

5. The process according to claim 4, characterized in that the surfactant from the group of $R^1$-(EO)$_n$-block-(PO)$_m$—$R^2$ where n is 4 to 12 and m is 3 to 12.

6. The process according to claim 4, characterized in that the surfactant from the group of $R^1$-(EO)$_n$-block-(PO)$_m$—$R^2$ where n is 5 to 8 and m is 4 to 7.

7. The process according to claim 4, characterized in that, for n and m in the formula $R^1$-(EO)$_n$-block-(PO)$_m$—$R^2$, more preferably, $2 \leq m \leq n \leq 20$.

8. The process according to claim 4, characterized in that the $R^1$ or $R^2$ radicals are allyl or acetyl and $R^1$ and/or $R^2$ are a methyl, ethyl, n-propyl, isopropyl, n-butyl, isobutyl, n-pentyl, 2-methylbutyl, 2,2-dimethylpropyl, —OH, acetyl or allyl radical.

9. The process according to claim 4, characterized in that $R^1$ or $R^2$ is an allyl radical and the other radical is an acetyl or —OH radical.

10. The process according to claim 1, characterized in that the surfactant and the blowing agent are added together to the monomer solution.

11. The process according to claim 1, characterized in that the blowing agents consist of a powder of inorganic particles.

12. The process according to claim 1, characterized in that the blowing agents consist of sodium carbonate particles.

13. The process according to claim 1, characterized in that the blowing agent has a particle size of 10 µm to 900 µm.

14. The process according to claim 1, characterized in that more than 35% by weight of the blowing agents have a particle size of 100-300 µm.

15. The process according to claim 1, characterized in that the permeability, as the Saline Flow Conductivity, SFC (1.5 g), is in the range from 30 to 200 units.

16. The process according to claim 4, characterized in that the $R^1$ and/or $R^2$ are a methyl, ethyl, n-propyl, isopropyl, n-butyl, isobutyl, n-pentyl, 2-methylbutyl, 2,2-dimethylpropyl, —OH, acetyl or allyl radical.

* * * * *